US007320859B2

(12) United States Patent
Schmidt et al.

(10) Patent No.: US 7,320,859 B2
(45) Date of Patent: Jan. 22, 2008

(54) MODULAR TRANSFECTION SYSTEMS

(75) Inventors: Hanns-Martin Schmidt, Köln (DE); Ludger Altrogge, Pulheim (DE); Dietmar Lenz, Köln (DE); Gudula Riemen, Langenfeld (DE); Helmut Brosterhus, Kirchundern (DE); Elke Lorbach, Köln (DE); Juliana Helfrich, Köln (DE); Katharina Hein, Köln (DE); Marion Gremse, Köln (DE); Tatjana Males, Hilden (DE); Rainer Christine, Köln (DE); Gregor Siebenkotten, Frechan-Königsdorf (DE); Bodo Ortmann, Köln (DE); Tamara Turbanski, Wiehl (DE); Andreas Klaes, Köln (DE)

(73) Assignee: Amaxa AG (DE)

( * ) Notice: Subject to any disclaimer, the term of this patent is extended or adjusted under 35 U.S.C. 154(b) by 197 days.

(21) Appl. No.: 10/466,368

(22) PCT Filed: Jan. 10, 2002

(86) PCT No.: PCT/DE02/00060

§ 371 (c)(1),
(2), (4) Date: Aug. 13, 2003

(87) PCT Pub. No.: WO02/055721

PCT Pub. Date: Jul. 18, 2002

(65) Prior Publication Data

US 2004/0137622 A1     Jul. 15, 2004

(30) Foreign Application Priority Data

Jan. 10, 2001   (DE) ............................... 101 00 996

(51) Int. Cl.
*C12Q 1/68*   (2006.01)

(52) U.S. Cl. .......................... 435/6; 435/455; 435/194; 530/350

(58) Field of Classification Search ...................... None
See application file for complete search history.

(56) References Cited

U.S. PATENT DOCUMENTS

| 4,950,599 A | 8/1990 | Bertling |
| 5,468,629 A | 11/1995 | Calhoun |
| 5,763,240 A | 6/1998 | Zarling et al. |

FOREIGN PATENT DOCUMENTS

| DE | 199 25 052 A | 12/2000 |
| WO | WO 95 34295 A | 12/1995 |

OTHER PUBLICATIONS

Ruponen et al., The Journal of Gene Medicine, vol. 6, 2004, pp. 405-414.*
Verma et al., Nature, vol. 389, 1997, pp. 239-242.*
Anderson, Nature, vol. 392 supplement, 1998, pp. 25-29.*
Juengst, BMJ, vol. 326, 2003, pp. 1410-1411.*
Feldherr, C.M., and Akin, D., "Regulation of Nuclear Transport in Proliferating and Quiescent Cells," (1993) *Experimental Cell Research* 205:179-186 (Exhibit 16).
Fominaya, J., and Wels, W., "Target cell-specific DNA transfer mediated by a chimeric multidomain protein," (1996) *J. Biol. Chem.* 271: 10560-10568 (Exhibit 17).
Griffith, J., et al., "Electron microscopic studies of the interaction between a *Bacillus subilis* alpha/beta-type small, acid-solube spore protein with DNA: protein binding is cooperative, stiffens the DNA, and induces negative supercoiling," (1994) *Proc. Natl. Acad. Sci. USA*. 91: 8224-8228 (Exhibit 8).
Harbottle, R.P., et al., "An RGD-oligolysine peptide:a prototype construct for integrin-mediated gene delivery," (1998) *Hum Gene Ther*. 9: 1037-1047 (Exhibit 19).
Hong, S. et al., "Cellular uptake and nuclear delivery of recombinant adenovirus penton base," (1999) *Virology*, 262:163-177 (Exhibit 20).
Karlin, S., et al., "Evolutionary conservation of RecA genes in relation to protein structure and function," (1996) *J. Bacteriol.* 178:1881-1894 (Exhibit 21).
Karlin, S., et al., "Bacterial classification derived from RecA protein sequence comparisons," (1995) *J. Bacteriol* 177: 6881-6893 (Exhibit 22).
Knight, K.L. and McEntee, K., "Affinity labeling of a tyrosine residue in the ATP binding site of the RecA from *Escherichia coli* with 5'-p-Fluorosulfonylbenzoyladenosine," (1985) *J. Biol. Chem.* 260:10177-10184 (Exhibit 23).
Kukowska-Latallo, J.F., et al., "Efficient transfer of genetic material into mammalian cells using Starburst polyamidoamine dendrimers," (1996) *Proc. Natl. Acad. Sci.* 93:4897-4902 (Exhibit 24).
Lee, C.K. and Knipe., "A Immunoassay for the study of DNA-binding activities of herpes simplex virus protein ICP8," (1985) *J. Virol*, 54: 731-738 (Exhibit 25).
Masson , J. U., et al., "The meiosis-specific recombinase hDmc1 forms ring structures and interactions with hRad51," (1999) *Embo. J*,. 18: 6552-6560 738 (Exhibit 26).

(Continued)

*Primary Examiner*—James Ketter
(74) *Attorney, Agent, or Firm*—Mandel & Adriano

(57) ABSTRACT

The present invention relates to a method for transfection of cells using at least one protein capable of forming nucleoprotein filaments, wherein the protein is initially modified with at least one functional component which influences one or more steps of the transfection, the nucleic acid to be transfected is then loaded with the modified protein, whereby the nucleic acid and the protein form a filament-like complex, and this complex is finally added to the cells to be transfected. The invention further relates to a transfection agent consisting of nucleoprotein filaments (NPF), with at least one nucleoprotein filament-forming protein being modified with at least one functional component for the transfection. Furthermore, the present invention relates to the use of the transfection agent according to the invention for producing a drug for gene therapeutic treatment of humans and animals. The present inventions also includes corresponding pharmaceutical preparations, especially for use in gene therapy as well as the use of such transfection agents as component in kits.

15 Claims, 24 Drawing Sheets

OTHER PUBLICATIONS

Figure 1:
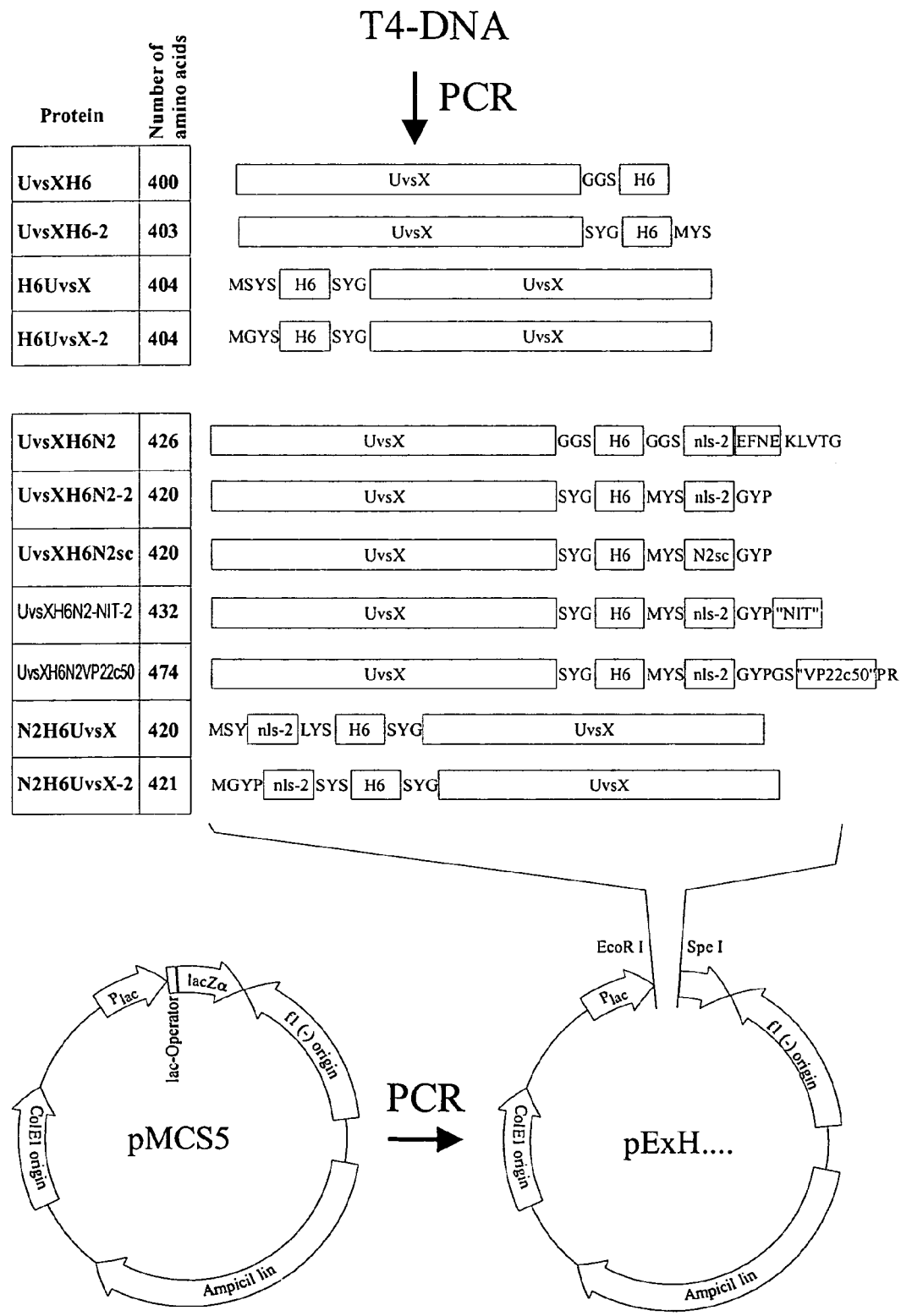

Mengaud, J., et al., "E-Cadherin is the receptor for internalin, a surface protein required for entry of *L. monocytogenes* into epithelial cell," (1996) *Cell* 84, 923-932 (Exhibit 27).

Midoux, P. et al., "Specific gene transfer mediated by lactosylated poly-L-lysine into hepatoma cells," (1993) *Nucleic Acids Res* 21:871-878 (Exhibit 28).

Mosig, G., "The essential role of recombination in phage T4 growth," (1997) *Annu. Rev. Genet.* 21: 347-371 (Exhibit 29).

Neumann, G., et al., "Nuclear import and export of influenza virus nucleoprotein," (1997) *J. Viorl.* 71:9690-9700 (Exhibit 30).

Tang, M.X., and Szoka, F.C., "The influence of polymer structure on the interactions of cationic polymers with DNA and morphology of the resulting complexes," (1997) *Gene Ther.* 4: 823-832 (Exhibit 46).

Thoren, P.E., et al., "The antennapedia peptide penetratin translocates across lipid bilayers- the first direct observation,"(2000) *FEBBS Lett.* 482: 265-268 (Exhibit 47).

Thyagarajan, B., et al., "Mammalian mitochondria posses homologous DNA recombination activity," (1996) *J. Biol. Chem.*, 271: 27536-27543 (Exhibit 48).

Wagner, E., "Application of membrane-active peptides for nonviral gene delivery,"(1999) *Adv. Drug Deliv. Rev.* 38: 279-289 (Exhibit 49).

Wang, P., et al., "The NPI-1/NPI-3 (karyopherin alpha) binding site on the influenza a virus nucleoprotein NP is a nonconventional nuclear localization signal," (1997) *J. Virol.* 71: 1850-1856 (Exhibit 50).

Weisbart, R.H., "Novel protein transfection of primary rat cortical neurons using an antibody that penetrate living cells," (2000) *J. Immunol.*, 164:6020-6026 (Exhibit 51).

Yamada, M., and Kasamatsu, H., "Role of nuclear pore complex in simian virus 40 nuclear targeting," (1993) *J. Virol.*, 67: 119-130 (Exhibit 52).

Yu, X., and Egelman, E.H., "DNA conformation induced by the bacteriophage T4 UvsX protein appears identical to the conformation induced by the *Escherichia coli* RecA protein,"(1993) *J. Mol. Biol.* 232: 1-4 (Exhibit 53).

Zauner, W., "Rhinovirus-mediated endosomal release of transfection complexes," (1995) *J. Virol.*, 69: 1085-1092 (Exhibit 54).

Bertolotti, R., "Recombinase-DNA nucleoprotein filaments as Gene Therapy vectors," (1998) *Biogenic Amines* 14:41-65 (Exhibit 55).

Kido, M. et al., "*Escherichia coli* RecA Protein Modified with a Nuclear Location Signal Binds to Chromosomes in Living Mammalian Cells," (1992) *Experimental Cell Research* 198:107-114 (Exhibit 56).

Anderson, K., "Codon Preferences in Free-Living Microorganisma," (1990) *Micobiol Rev.* 54: 98-210 (Exhibit 1).

Bal, H.P., et al., "Adenovirus type 7 penton purification of solube pentamers from *Escherichia coli* and development of an integrin-dependent gene delivery system," (2000) *Eur. J. Biochem.* 267: 6074-6081 (Exhibit 2).

Baumann, P., and West, S.C., "Role of the human RAD51 protein in homologous recombination and double-stranded-break repair," (1998) *Trends Biochem Sci.* 23: 247-227 (Exhibit 3).

Bianco, P. R., et al., "DNA strand exchange proteins: a biochemical and physical comparison," (1998) *Front Biosci.* 3: D570-603 (Exhibit 4).

Boulikas, T., "Nuclear localization signals (NLS)," (1993) *Crit Rev Eukaryot Gene Expr* 3:193-227. (Exhibit 5).

Boulikas, T., "Nuclear import of protein kinases and cyclins," (1996) *J. Cell Biochem.* 60: 61-82 (Exhibit 6).

Boulikas, T., "Nuclear import of DNA repair proteins," (1997) *Anticancer Res.* 17: 843-863 (Exhibit 7).

Cagnon, C., et al., "A new family of sugar-inducible expression vectors for *Escherichia coli*," (1991) *Protein Eng.* 4: 843-847 (Exhibit 8).

Cerutti, H., et al., "A homolog of *Escherichia cloi* RecA protein in plastids of higher plants," *Proc. Natl. Acad. Sci. USA* 89: 8068-8072 (Exhibit 9) (1992).

Collins, L., et al., "In itro investigation of factors important for the delivery of an integrin-targeted non-viral DNA vector in organ transplantation," *Transplantation.* 69: 1168-1176 (Exhibit 10) (2000).

Declayre, A.X., et al., "Epstein Barr Virus/ complement C3d receptor is an interferon alpha receptor," (1991) *Embo. J.* 10: 919-926 (Exhibit 11).

Di Capua, E., et al., "Characterization of complexes between recA protein and duplex DNA by Electron microscopy," *J. Mol Biol.* 157: 87-103 (Exhibit 12) (1982).

Ellouze, C., et al., "Difference between active and inactive nucleotide cofactors in the effect on the DNA binding and the helical structure of RecA filament, Dissocation of RecA—DNA complex inactive nucleotides," *Eur. J. Biochem.* 262: 88-94 (Exhibit 13) (1999).

Evan, C., et al., "Isolation of Monoclonal antibodies specific for human c-myc proto- oncogene product," *Mol. Cell Biol.* 5: 3610-3616 (Exhibit 14) (1985).

Feero, W.G., et al., "Selection and use of ligands for receptors-mediated gene delivery to myogenic cells," (1997) *Gene Ther.* 4: 664-674 (Exhibit 15).

Ogawa, T., et al., "RecA-like recombination proteins in eukaryotes: functions and structures of *RAD51* genes," (1993) *Cold Spring Harb Symb Quant Biol.* 58: 567-576 (Exhibit 31).

Ohno, K., et al., "Cell-specific targeting of Sindbis virus vectors displaying IgG-binding domains of protein A," (1997) *Nat. Biotechnol.* 15: 763-767 (Exhibit 32).

Pack, D., et al., "Design of imidazole-containing endosomolytic biopolymers for gene delivery," (2000) *Biotechnol Bioeng.* 67: 217-223 (Exhibit 33).

Plow, E. F., et al., "Ligand binding to integrins," (2000) *J. Biol. Chem.* 275 : 1-22 (Exhibit 34).

Pooga, M., et al., "Cell penetrating PNA constructs regulate galanin receptor levels and modify pain transmission in vivo," (1998) *Nat. Biotechnol.* 16: 857-861 (Exhibit 35).

Provoda, C.J., "Bacterial pore-forming hemolysins and their use in the cytosolic delivery of macromolecules," (2000) *Adv. Drug Deliv. Rev.* 41: 209-221 (Exhibit 36).

Richardson, S., et al., "Poly(amidoamine)s as potential endosomolytic polymers: evaluation in vitro and body distribution in normal and tumor-bearing animals," (1999) J. Drug Target 6: 391-404 (Exhibit 37).

Roca, A.I., and Cox, M.M., "The RecA protein: structure and function," (1990) *Crit. Rev. Biochem Mol. Biol.* 25: 415-456 (Exhibit 38).

Rosenkranz, A. A., et al., "Receptor-mediated endocytosis and nuclear transport of a transfecting DNA construct," (1992) *Exp. Cell Res.* 199: 323-329 (Exhibit 39).

Sandler, S. J. et al., "RecA-like genes from three archaean species with putative protein products similar to Rad51 and Dmc1 proteins of the yeast *Saccharomyces cerevisiae*," (1996) *Nucleic Acids Res.* 24: 2125-2132 (Exhibit 40).

Schagger, H. et al., "Tricine-sodium Docecyl Sulfate-polyacrylamide gel Electrophoresis for the separation of Proteins in the Range from 1 to 100 kDa," (1997) *Anal Biochem* 166:368-379 (Exhibit 41).

Schoeman, R., et al., "Further studies on targeted DNA transfer to cells using highly efficient delivery system of biotinylated trasferrin and biotinylated polylysine complexed to streptavidin," J. Drug Target., 2:509-516 (Exhibit 42) (1995).

Seitz, E. M., et al., "RadA protein is an archaeal RecA protein homolog that catalyzes DNA strand exchange," (1998) *Genes Dev.* 69: 6643-6651 (Exhibit 43).

Steinhauer, D.A., et al., "Studies of the membrane fusion activities of fusion peptide mutants of influenza virus hemagglutinin," (1995) *J. Virol.* 69: 6643-6651 (Exhibit 44).

Surdej, P., and Jacobs-Lorena, M., "Strategy for epitode tagging the protein-coding region of any gene," (1994) *Biotechniques* 17, 560-565 (Exhibit 45).

\* cited by examiner

NIH3T3 cells
pH-2K$^k$/ATPγS

NIH3T3 cells
pH-2K$^k$/UvsX/ATPγS

NIH3T3 cells
pH-2K$^k$/UvsX-NLS/ATPγS

UvsXH6N2NIT-2

↘▲ vesicular compartment with endocytosed NPFs

UvsXH6N2-2

↘▲ vesicular compartment with endocytosed NPFs

SEQUENCE LISTING

<160> NUMBER OF SEQ ID NOS: 9

<210> SEQ ID NO 1
<211> LENGTH: 14
<212> TYPE: PRT
<213> ORGANISM: Artificial
<220> FEATURE:
<223> OTHER INFORMATION: scrambled sequence of nls-2(amino acids 2-15 of SEQ ID No. 9 in WO 00/40742), i.e. same amino acids but different sequence

<400> SEQUENCE: 1

Glu Lys Pro Glu Lys Asp Lys Glu Pro Arg Thr Lys Val Asp
1               5                   10

<210> SEQ ID NO 2
<211> LENGTH: 29
<212> TYPE: DNA
<213> ORGANISM: Artificial
<220> FEATURE:
<223> OTHER INFORMATION: Example 1: Additional 5' nucleotides sequences of PCR products

<400> SEQUENCE: 2
cacacagaat tcataaagga agatatcat                                         29

<210> SEQ ID NO 3
<211> LENGTH: 12
<212> TYPE: DNA
<213> ORGANISM: Artificial
<220> FEATURE:
<223> OTHER INFORMATION: Example 1: Additional 3' nucleotide sequences of PCR products

<400> SEQUENCE: 3
actagttgtg tg                                                           12

<210> SEQ ID NO 4
<211> LENGTH: 14
<212> TYPE: PRT
<213> ORGANISM: Artificial
<220> FEATURE:
<223> OTHER INFORMATION: nls-2: corresponds to amino acids 2-15 of SEQ ID NO. 9 from WO 00/40742

<400> SEQUENCE: 4

Glu Glu Asp Thr Pro Pro Lys Lys Lys Arg Lys Val Glu Asp
1               5                   10

<210> SEQ ID NO 5
<211> LENGTH: 12
<212> TYPE: PRT
<213> ORGANISM: Artificial
<220> FEATURE:
<223> OTHER INFORMATION: amino acids 421-432: RDG motif NIT

<400> SEQUENCE: 5

Asn Ile Thr Arg Gly Asp Thr Tyr Ile Pro Tyr Pro
1               5                   10

<210> SEQ ID NO 6
<211> LENGTH: 26
<212> TYPE: DNA
<213> ORGANISM: Artificial
<220> FEATURE:
<223> OTHER INFORMATION: Example 11: additional 5' sequences of PCR -continued

```
products

<400> SEQUENCE: 6
cacacatcta gacgtacgga tatcat                                              26

<210> SEQ ID NO 7
<211> LENGTH: 30
<212> TYPE: DNA
<213> ORGANISM: Artificial
<220> FEATURE:
<223> OTHER INFORMATION: Example 11: additional 3' sequences of PCR
      products

<400> SEQUENCE: 7
tactcgtacg gaggtggcgg ccgctgtgtg                                          30

<210> SEQ ID NO 8
<211> LENGTH: 20
<212> TYPE: DNA
<213> ORGANISM: Artificial
<220> FEATURE:
<223> OTHER INFORMATION: Example 12: additional 5' sequences of PCR
      products

<400> SEQUENCE: 8
cacacaggta cccgggatcc                                                     20

<210> SEQ ID NO 9
<211> LENGTH: 35
<212> TYPE: DNA
<213> ORGANISM: Artificial
<220> FEATURE:
<223> OTHER INFORMATION: Example 12: additional 3' sequences of PCR
      products

<400> SEQUENCE: 9
cctaggtaat aataagcggc cgcgctagct gtgtg                                    35
```

MODULAR TRANSFECTION SYSTEMS

This application claims the priority of German application No. 101 00 996.8, filed Jan. 10, 2001, and PCT application No. PCT/DE02/00060, filed Jan. 10, 2002, the contents of which are hereby incorporated by reference in their entirety into this application.

BACKGROUND OF THE INVENTION

The present invention relates to the field of non-viral transfection of nucleic acids. The term transfection generally means the introduction of foreign substances into cells. The present invention relates to a method for the transfection of cells with the help of at least one protein which is capable of forming nucleoprotein filaments. The invention also relates to a transfection agent which contains a nucleoprotein filament (NPF) which is formed from at least one nucleic acid to be transfected and at least one protein which is capable of forming nucleoprotein filaments. In addition, the present invention relates to the use of the transfection agent according to the invention, a corresponding pharmaceutical formulation, in particular for use in gene therapy, a kit for the transfection of cells with nucleic acids and particular methods which use the transfection agent according to the invention.

STATE OF THE ART

The known non-viral transfection agents are subject to a series of restrictions. In non-viral transfection of nucleic acids, both the size of the globular nucleic acid complexes, which are often unilaterally charged, and the lack of controllability of one or several transfection steps are usually a major problem. One cause of the latter is the inadequate ability to penetrate the external cell membrane or the membranes of internal compartments, inadequate protection from enzymatic degradation, low bioavailability and biological effects of inadequate controllability caused by non-biological molecules in the cell. Nucleic acids mostly contain highly expanded steric structures, are easily degradable by enzymes, and their unilateral charge excess causes ready association with basic cell structures. The associated inadequate ability to pass into the nucleus has the result that the current nucleic acid transfection technologies almost exclusively employ cancer-like transformed cells, such as cell lines, as the nuclear membrane in these cells is temporarily disintegrated during cell division and entry into the nucleus is possible. However, transformed cells are not comparable to the original physiological state of primary cells, so that conclusions about the behavior of primary transfected cells cannot be reliably based on studies using transformed cells.

A series of transfection agents is already known, almost all of which form globular complexes with nucleic acids by electrostatic interaction, often with a diameter of more than 50 nm (Tang and Szoka, 1997). These complexes mostly associate at the cell surface with a large excess of charge and are taken up by endocytosis. They leave the endosomes, either by buffering the acidification of the endosomes until these burst (e.g. with polyethylenimine, starburst dendrimers (Kukowska-Latello et al. 1996) or addition of chloroquine), or by the action of membrane-active groups, lipids or lipophilic peptides. However, the complexes can only reach the cell nucleus during the next cell division to show there the desired effects after the nucleic acid has been released.

The problem of the division-dependent nuclear import can be avoided by the use of NLS-peptides (NLS=nuclear localization signal), particularly when attention is paid to the problems of signal masking and non-specific protein binding (WO 00/40742, Amaxa).

U.S. Pat. No. 5,468,629 describes the use of the RecA protein and the possible use of other proteins with functional homology to RecA in the transfection of cells with ssDNA (single-strand DNA). The protein RecA supports, evidently by catalysis, the process of homologous recombination of the transported ssDNA with the cell DNA by influencing strand pairing and the subsequent strand exchange. The complexes used here contain ssDNA of maximally 700 nucleotides as well as RecA protein and are described as "RecA-coated" complexes. Such ssDNA-protein complexes are formed from DNA in the presence of RecA and ATP-γ-S, with the formation of stable helical presynaptic filaments. These complexes are used with little success, for example, for the transfection of cell lines, i.e. for actively dividing cells, in particular transformed cells.

SUMMARY OF THE INVENTION

It is the object of the present invention to provide a method and a transfection agent for the transfection of nucleic acids of any sort into cells of any sort, which permit improved uptake in cells and which at the same time allows the control of the transfection process. The transfection agent for this purpose should both be adequately stable during the transfection process and also guarantee adequate release of the nucleic acids to be transfected in the target cell compartment.

This object is solved according to the invention with a method of the type mentioned in the introduction, wherein the protein is initially modified with at least one functional component which influences one or more steps of the transfection. The nucleic acid to be transfected is then loaded with the modified protein, the nucleic acid and the protein forming a filament-shaped complex, and this complex is finally added to the cells to be transfected.

In addition, this object is solved by a transfection agent of the type mentioned in the introduction, wherein the protein that is capable of forming nucleoprotein filaments is modified with at least one component influencing the transfection.

As a result of the modification of one or several proteins which form nucleoprotein filaments (NPF) with one or several of the same or different additional functional components, individual steps of the complex transfection process can be controlled in a particularly advantageous manner which is specific for the nucleic acid to be transfected and for the target cell. In addition, the method and transfection agent according to the invention permit a clear increase in transfection efficiency in comparison with known methods.

According to the invention, the NPF-forming proteins are used in an advantageous manner, particularly as modular carrier system for functional groups, which goes beyond pure protection of DNA. The complex exhibits very low extension in space in two respects: it is filamentous—not globular—and it contains only one nucleic acid molecule per filament. Because of the assembly which leads to a stochiometric ratio of a few nucleotides per carrier protein, an extremely high density of functional signals for transfection is possible, much more than with globular complexes. The signal density and also the combination of different signals can be individually adjusted by the mixture of different functionalized carrier proteins and proteins without functional groups, so that the transfection agent according to the invention can be designed as a modular system for the widest variety of transfection conditions. The low extension in space and the high signal density also make it possible to use in addition endogenous transport systems which are specific for small molecules. Because of its filamentary character, its simple structure and its is adjustable and extremely high signal density, the method according to the invention makes possible, or the transfection agent according to the invention is capable of, specifically transporting of larger nucleic acid molecules, such as expression vectors, using endogenous mechanisms.

The additional functional components can for example be bound directly to the NPF proteins or via a spacer, a non-functional separating unit. Spacers of this kind give rise to a greater distance between the NPF and the functional components, which avoids mutual steric hindrance and which guarantees better spatial availability of the NPF protein and of the functional components. The structure of the agents according to the invention thereby then largely avoids masking of the functional components.

NPF-forming proteins form nucleoprotein filaments with nucleic acids mostly by cooperative binding, in which proteins and nucleic acids form a complex having a size or diameter that is much smaller than that of the known globular transfection agents. An NPF of this kind can for example be formed by proteins of the RecA family, which are DNA-dependent ATPases, in the presence of nucleoside triphosphates such as ATP (adenosine triphosphate), with total loading of a density of, for example, one protein per three bases in double-stranded DNA (Bianco et al., 1998). This high protein density offers excellent protection against enzymatic hydrolysis of the nucleic acids as the possible points of enzymatic attack are greatly reduced. The NPF not only causes the complex to be adequately stable but also allows adequate release of the transported nucleic acids, for example, in the nucleus. Use of non-hydrolyzable or poorly hydrolyzable analogues of nucleoside triphosphates, for example of ATP and/or GTP, such as ATP-γ-S or GTP-γ-S, also offers the possibility of providing extra stability to NPFs which are formed with ATP-forming proteins, such as the RecA family.

According to the invention, the proteins capable of forming NPFs also include derivatized NPF proteins. For example, fusion proteins can be produced. In addition, NPF-forming proteins can be truncated or elongated, individual sections or amino acids can be deleted, introduced or chemically modified as long as their function which is essential to the invention, the structural formation of NPFs with nucleic acids, is maintained.

A particular advantage of the invention is the spatial structure of the NPFs which makes it possible to exploit the natural mechanisms of nuclear transport. The maximal diameter of the transfection agent is determined by the size of the nuclear pores and is not exceeded even with very long nucleic acids, i.e. NPFs can be used as transfecting agents independently of the length of the nucleic acid to be transfected. It has been shown that the size limit for transport through the nuclear pore is approx. 25 nm (Feldherr and Akin, 1997) or 50 nm (SV40-Virus) (Yamada and Kasamatsu, 1993). Nucleic acids, of which the import through the nuclear membrane with conventional transfection agents having globular structure and/or non-specific binding of several nucleic acid molecules per transfection component is barred, can easily lie under such limit using transfection agents according to the invention. The structure of the transfection agents according to the invention even makes it possible to use for the first time diameters of $\leq 11$ nm, depending on the NPF-forming protein used. The filamentous structure assembled by the use of NPF proteins is therefore also suitable for the transport of longer nucleic acids of several kilobases in length. The method according to the invention and the transfection agents according to the invention are consequently particularly well suited for the transfection of cells with larger nucleic acid sequences. Transfection agents according to the invention are preferred which contain a nucleic acid to be transfected including at least 700 nucleotides.

The present invention can advantageously be used as such for the transfection of nucleic acids or in combination with other transfection methods and materials. The high degree of loading with NPF-forming proteins increases the stability to hydrolysis and the low diameter of the NPF allows the exploitation of endogenous cellular transport mechanisms which are only available to molecules which are small enough, for example, those of the nuclear transport system. In addition, adequate release of the nucleic acids to be transfected in the cell compartments, preferably in the nucleus, is guaranteed.

The term "transfection agent" according to the invention is to be understood as transport vehicle for nucleic acids or their derivatives which already contain the nucleic acid to be transfected. A transfection agent in the sense of the invention performs at least a single step of the complex process of transfection.

In the context of the present invention, the term "nucleoprotein filament" (NPF) means a molecular structure consisting of nucleic acid(s) or nucleic acid derivatives and proteins which, as the result of non-covalent, mostly cooperative binding, form a filamentary or thread-like complex which preferably contains only a single nucleic acid molecule or derivative of this. Particularly preferred are helical nucleoprotein filaments, for example, those formed from RecA with single or double-stranded DNA (Di Capua et al., 1982).

The "nucleic acid to be transfected" can be either a double or a single-stranded DNA, or a double- or single-stranded RNA, or a double-stranded DNA with single-stranded ends, a DNA/RNA hybrid, an antisense DNA, antisense RNA or chemically modified nucleic acid derivatives, in which, for example, the resistance to hydrolysis is increased (pepide nucleic acid, PNA), or in which reactive molecular groups have been introduced for the covalent binding and/or the modification of target nucleic acids. Derivatives of transfectable nucleic acids are understood to include the modification of the nucleic acid used with a sequence-specific or covalently bound protein. The preferred nucleic acid of the present invention is DNA, in particular, double-stranded DNA. Until now, NPF-forming proteins have mostly been used together with single-stranded DNA, for example, for recombination. Surprisingly, it has turned out in the context of the invention that many NPF-forming proteins also form stable complexes with double-stranded DNA under suitable conditions and can be used for the transfection of double-stranded DNA in accordance with the invention. It is therefore a further advantage of the invention that efficent transfection with double-stranded DNA is possible too.

In an advantageous embodiment of the invention, NPFs modified with functional components are produced by the modification of original NPF-forming proteins or their derivatives. This modification can be the deletion or insertion of amino acids and/or protein domains. The modification can also be provided by chemical alteration of amino acids and/or other molecular groups and/or by chemical coupling of peptides, proteins, carbohydrates, lipids or other molecules to the NPF-forming protein or its derivative.

These modifications may occur with the use of a spacer.

The first hurdle for transfection consists in the association of the transfection complex to the cell surface. A preferred embodiment of the method and transfection agent according to the invention therefore uses at least one protein capable of forming NPF which is modified with at least one functional group which causes the association of the complex or agent to the cell surface. This can be performed specifically for the cell type by binding to surface structures specific to the cell type which are expressed on one or only a few cell types, or non-specifically, for example, by an electrostatic interaction. All naturally occurring or synthetically produced substances can be used for the cell type-specific binding which bind to receptors on the cell surface, such as receptors which are used by viruses or bacteria for cell entry, e.g. the Epstein Barr Virus receptor CD21 (Delcayre, 1991) or *Listeria monocytogenes* receptor E-cadherin (Mengaud, 1996). Other examples for the use of ligand-receptor pairs include the transferrin receptor/transferrin system for cells which need a lot of iron, asialoglycoprotein receptor/galactose for hepatocytes, integrin/integrin-binding peptides, such as RGD (Harbottle 1998) or molossin (Collins 2000) or hormones which bind to hormone receptors, such as insulin (Rosenkranz 1992), EGF (epidermal growth factor) or insulin-like growth factor I (Feero, 1997) and oligosaccharides which bind to lectins (Midoux et al., 1993). It is also possible to use cell-specific antibodies (Fominaya, 1996) or protein A or its IgG-binding domain (Ohno, 1997) as well as biotinylated proteins (either proteins biotinylated on the cell surface or biotinylated monoclonal antibodies) in combination with streptavidin (Schoeman, 1995). It is particularly suitable in the context of the present invention to use "epitope tagging", i.e. cell type specific transfection using biospecific antibodies which, on the one hand can recognize an epitope, namely short peptides such as from the influenza hemagglutinin (Surdej, 1994) or from the c-myc protein (Evan, 1985) which are either coupled or fused by genetic engineering to the NPF-forming proteins or their derivatives and, on the other hand, to specific cell surface structures. For non-cell specific interactions of the transfection complex by electrostatic forces it is possible, for example, to introduce positive charges with additional amino acids (lysine, arginine, histidine).

In another particularly preferred embodiment of the method and transfection agent according to the invention, it is intended that the functional components cause the non-endosomal passage of the complex or agent through the cell membrane. The non-endosomal membrane passage has the advantage that the agent is immediately available in the cytosol and is not exposed to the hydrolytically active environment of the lysosomes. Membrane passage of this kind can be attained with membrane-active molecules. These can be naturally occurring, modified or synthetic peptides which are mostly aliphatic or amphiphilic, such as viral peptides, for example HIV tat, VP22, HBV surface antigen; peptides from transcription factors such as, for example, the homeodomain of antennapedia (Thoren et al 2000), engrailed, HOXA-5; peptides from cytokines, e.g. IL-1β, FGF-1, FGF-2; peptides from cellular signal sequences, e.g. the Kaposi fibroblast growth factor, monoclonal antibodies which penetrate living cells, e.g. mab 3E10 (Weisbart et al 2000), synthetic or chimeric peptides, e.g. amphiphilic model peptides or transportane (Pooga et al. 1998).

In addition, an advantageous embodiment of the invention uses at least one functional component according to the invention which causes the release of the complex or agent from endosomes or lysosomes. For example, passage through the cell membrane can occur through endocytosis. After endocytosis, the nucleoprotein complexes must be released from the endosomes. For this purpose, all substances with endosomolytic activity can be used. These can, for example, be peptides, their derivatives or synthetic analogues from bacteria or viruses, or other synthetic substances known to the person skilled in the art. Endosomolytic substances from bacteria include, for example, streptolysin O, pneumolysin, staphylococcal α-toxin, listeriolysin O (Provoda, 2000). Viral peptides include, for example, the N-terminal hemagglutinin HA-2 peptide of influenza virus (Steinhauer et al., 1995), the N-terminus of the VP-1 protein of rhinovirus HRV2 (Zauner et al., 1995) or the capsid component Ad2 of adenovirus (Hong, 1999). Synthetic substances include, for example, amphipathic peptides (GALA, KALA, EGLA, JTS1) (Wagner, 1999) or imidazole-(Pack, 2000) or polyamidoamine-modified polymers (Richardson, 1999).

Passage (import) into the nucleus occurring usually in dependence on cell division and possibly after stimulation of the cell is a particular hurdle for all transfection agents. It is therefore intended in a particularly advantageous embodiment of the invention to use a functional component which causes the transport of the complex or agent into the cell nucleus. The essentials in nuclear transport are firstly the limiting diameter of the nuclear pores and secondly the signal molecules used for transport.

The signals for nuclear transport in the context of the invention are nuclear ligands which bind to a nuclear receptor. Particularly suitable nuclear ligands are NLS (nuclear localization signals) or other components of the nuclear transport machinery. The nuclear localization signals which are particularly preferred for use are those signals which either themselves and/or together with their flanking regions exhibit little or no positive charge excess, as a charge excess can lead to non-specific nucleic acid binding and thus to masking of the signal. Well suited are extended sequences of so-called classical NLS when the total charge of the peptide can be at least approximately balanced by flanking negatively charged amino acids. These amino acids can occur naturally in the peptide/protein in these positions or be introduced there on the basis of structural considerations. The so-called non-classical NLS can also be used, for example, an NLS from the influenza virus "nucleoprotein" (Wang et al., 1997, Neumann et al., 1997) or the sequence M9 from the heterogenous nuclear RNP (hnRNP) A1 protein which have no great excess of positive charges or which pass into the nucleus by a non-classical transport route. An incomplete but good review of the NLS which can be used in the embodiment of the present invention is given by T. Boulikas (1993, 1996, 1997). Approximately charge-neutral sequences include, for example, the large T-antigen from simian virus 40 having flanking negative charges which are either naturally occurring or artificially introduced (see also WO 00/40742 Amaxa).

A particular advantage of the invention is therefore the clear improvement of the transfection of nucleic acids of eukaryotic cells which are either not dividing or only dividing weakly, in paticular primary eukaryotic cells. It is exactly these cells which have not yet forfeited their ability to provide biological or medical information, as they can, for example, be taken directly from the body by blood sampling or tissue biopsy and are of decisive importance to the skilled person. With the expected analysis of the almost completely decoded human genome, it is only the specific expression of the gene being examined in cell systems which will finally give clear evdience of possible technical applicability with adequate physiological relevance. In addition, the transfection of primary cells is an essential precondition for non-viral gene therapy, both ex vivo and in vivo.

In an advantageous embodiment of the invention, the method and transfection agent according to the invention can each include at least one protein being capable of forming nucleoprotein filaments which is modified with several functional components of different function and/or different proteins which are modified with proteins of different function, respectively. The transfection agents according to the invention can, as described above, be realized with a plurality of proteins which can form NPFs or derivatives thereof which may be present in their original or in a functionally modified form. Either a single or several different proteins which can form NPFs may be used and these can be modified with one or several functional components of the same or different functions, depending on the specfic requirements of the transfection. Depending on the intended goal, different modules can be assembled by the user in this way. This gives rise to a modular system from which unmodified or modified NPF proteins of the same or different function can be selected in order to achieve an optimal adaptation of the transfection strategy to the nucleic acid to be transfected and the target cell.

A particularly advantageous embodiment of the invention is intended, in which the protein is loaded with a plurality of functional components. In this way, the total signal density can be still further increased, so that improved transfection efficiency and better control of transfection are possible.

Many NPF-forming proteins form the NPF structure in the presence of nucleoside triphosphates, such as ATP, as cofactor. The addition of nucleoside triphosphates hereby stabilizes the NPF. In the method according to the invention, the NPF structure can therefore be advantageously formed or stabilized by nucleoside triphosphates and/or non-hydrolyzable analogues of these, in particular with ATP (adenosine triphosphate) and/or GTP (guanosine triphosphate) and/or their non-hydrolyzable analogues. This can also occur by covalent binding after a photochemical reaction. Non-hydrolyzable nucleoside triphosphate analogues include, for example, ATP-γ-S (adenosine 5'-O-3-thiotriphosphate) and GTPγS (guanosine 5'-O-3-thiotriphosphate) (Ellouze, 1999). Possible ATP analogues which modify NPF-ATPases after a photochemical reaction include $8N_3ATP$ (8-azidoadenosine 5'-triphosphate) and 5'FSBA (5'-p-fluorosulfonylbenzoyladenosine) (Knight, 1985).

In an advantageous embodiment of the method according to the invention, this is used in combination with other biological and/or chemical and/or physical transfection methods for biologically active molecules, such as liposome-mediated transfer, microinjection, electroporation, immunoporation, the ballistic method, transfer with the help of cationic lipids, calcium phosphate, DEAE-dextran, polyethylenimine or pH-sensitive hydrogel. Transfer methods of this sort, in particular electroporation, can advantageously support individual steps in the transfection process, for example, such as the import into the cytoplasm of the cell.

Preferred transfection agents according to the invention include as NPF-forming protein a protein selected from the group of proteins containing RecA, RadA, ScRad51, RAD51, hDmc1, SASP, ICP8, preferably UvsX, more preferably hRAD51 or a mixture of at least 2 of the proteins in this group or one or several derivatives of these proteins. NPF-forming proteins for the embodiment of the present invention include for example RecA from *Escherichia coli* and its functional homologues from viruses, prokaryotes and eukaryotes, such as UvsX from the bacteriophage T4 (Mosig, 1987), RadA from archebacteria (Seitz et al., 1998), ScRad51 from *Saccharomyces cerevisiae*, RAD51 from mammals and, in particular, hRad51 from man. e.g., varient 1 nucleotide and amino acid sequence describe in NCBI accession no. NM_002875; varient 2, nucleotide and amono acid sequence in NCBI accession no. $NM_{13}$ 133487. Homologous proteins to RecA have been detected in at least 60 different sorts of bacteria (Roca and Cox, 1990, Karlin and Brocchieri, 1996, Karlin et al., 1995), in archaea (Sandler et al. 1996), in all eukaryotes which have been examined (Ogawa et al. 1993), in mitochondria (Thyagarajan et al., 1996) and in plastids (Cerutti et al., 1992). With single- or double-stranded DNA, RecA and its homologues form helical NPF with a diameter of about 11 nm. The binding of RecA is cooperative and leads to a partial unwinding of the DNA helix. RecA, UvsX, ScRad51 and hRad51 form NPF with a binding stoichiometry of three base pairs per monomer (double-stranded DNA) or 3-6 nucleotides per monomer (single-stranded DNA) (Bianco et al. 1998, Baumann and West 1998). The meiosis-specific recombinase hDMC1 is preferred; this forms filaments with double-stranded DNA which consist of a linear row of stacked protein rings (Masson et al., 1999). In addition, the group of SASP proteins (small acid-soluble spore proteins) from the spores of *Bacillus* and *Clostridium* species is also preferred. The SASPs also bind to double-stranded DNA forming helical NPF with a diameter of about 6.6 nm (Griffith et al. 1994). Viral proteins which can form filaments with single- and/or double-stranded DNA, such as protein ICP8 from *Herpes simplex*, are also preferred as NPF-forming proteins (Lee & Knipe, 1985).

A binding stochiometry of one monomer protein per 3 base pairs has been demonstrated for complete binding of the NPF-forming proteins UvsX, Rad51 and RecA to double-stranded DNA (Bianco et al 1998). Complete binding of this kindcan be attained with UvsX, for example, by using a 3- to 5-fold excess of the protein, depending on the binding buffer used, the conformation of the nucleic acid and the temperature (Yu and Egelman 1993); with α/β type SASP from *Bacillus subtilis* the corresponding protein:DNA ratio is about 5:1 (Griffith et al 1994). It is particularly preferred in the context of this invention for the loading of the nucleic acid with protein to be as complete as at all possible; this is defined separately for each of the preferred NPF-forming proteins. However, incomplete loading of the nucleic acids below the absolutely highest degree of loading for a specific NPF-forming protein is possible in the context of the invention. Lower loading of the nucleic acids with NPF-forming proteins is, for example, preferred when additional DNA-binding proteins are to be used for defined steps in the transfection or when buffer conditions have to be selected for specific applications which are not optimal for complete loading of the nucleic acid with NPF-forming proteins.

According to the invention, NPF-forming proteins are understood to include both natural NPF-forming proteins and their derivatives. Under derivatives of NPF-forming proteins, the skilled person understands firstly modification by deletion or insertion of additional amino acid sequences or protein domains in recombinant proteins and/or the introduction of functional groups by the chemical modification of molecular groups which are already present and/or the chemical coupling of proteins, peptides, carbohydrates, lipids or other molecules.

The transfection agent according to the invention can also be advantageously used for producing drugs for the gene therapeutic treatment of humans and animals. The therapeutically useful nucleic acids can be made accessible to primary cells and complex transfection methods in the form of transfection agents according to the invention.

A further aspect of the present invention concerns pharmaceutical preparations which contain a transfection agent according to the invention, possibly together with conventional adjuvants and carriers.

A further aspect of the present invention concerns kits which are suitable for the transfection of cells with nucleic acids and which include at least one protein capable of forming NPFs according to the invention and at least one functional component according to the invention as well as at least one of the following components:

a) nucleoside triphosphate and/or nucleoside triphosphate analogues b) at least one nucleic acid to be transfected c) adjuvants and additives Such kits can be specifically designed for the different requirements of experts, for example, they can be optimized for certain nucleic acids, target cells or stability requirements, by the selection of specific NPFs, specific NPF modifications or individual adjuvants or additives. The protein can hereby already be loaded with the functional component(s) or the proteins or functional components can be contained separately in the kit.

A further aspect of the present invention concerns the use of the transfection agents according to the invention for cell screening, specifically for the identification of activators or inhibitors of the expression product(s) of the transfection agent in mitotically inactive or weakly active cells, primary cells and other cells of limited life span. Screening of this kind is a fundamental method for the identification of activators or inhibitors of validated or non-validated target proteins in the identification of active substances in the pharmaceutical industry. These screening methods are usually planned so that cells which have been stably transfected with foreign nucleic acids are exposed to potential inhibitors and/or activators and the influence of these on the physiology of the cells is determined, possibly in comparison with comparator cells. The transfection agent according to the invention is suitable for the insertion of the foreign nucleic acid shortly before the addition of activators or inhibitors, even in mitotically inactive or only weakly active cells, primary cells and other cells of limited life span, and thus to make these cells accessible as test cells.

A further aspect of the present invention concerns the use of transfection agents according to the invention in the identification of physiologically active nucleic acids. This is of particular importance for the rapid and physiologically relevant evaluation of genomic data which are available to the scientific and pharmaceutical community. As transfection with the transfection agents according to the invention is independent of cell division and/or endocytosis, the time between transfection and analysis is much shortened. This makes a much higher sample throughput possible. Even cells which are difficult to transfect and even non-dividing cells are accessible with the transfection agents according to the invention. The resulting transfection and the physiological evaluation of changes in comparison to control cells make the identification of physiologically active nucleic acids possible.

ABBREVIATIONS

Aside from the abbreviations usual in Duden[1], the following abbreviations are used:

[1] Translator's Note: German Standard dictionary

AMP-PCP Adenylyl-(β,β-methylene)-diphosphonate
AMP-PNP 5'-Adenylylimidodiphosphate
DEAE Diethylaminoethane
DNA Desoxyribonucleic acid
dYT Double yeast trypton
FACScan Fluorescence activated cell scanning
FCS Fetal calf serum
FL Fluorescence
FSC Forward scatter
GMP-PNP 5'-Guanylylimidodiphosphate
GTP Guanosine triphosphate
H6 Histidine hexamer
Ig Immunoglobulin
kb Kilobases
ml Milliliter
mM Millimolar
msec Millisecond
NCBI National Center for Biology Information
ng Nanogram
nm Nanomolar
PBS Phosphate buffered salt solution
PCR Polymerase chain reaction
Pi Sodium dihydrogen phosphate/Disodium hydrogen phosphate
RNA Ribonucleic acid
RPMI Roswell Park Memorial Institute
SDS Sodium dodecylsulfate
SV40 Simian virus 40
TAE Tris-acetate/ethylend iaminetetraacetate
U/mg Units/Milligram
rpm Revolutions per minute
CI-Puffer Cell injection buffer
µg Microgram
µl Microliter

SHORT DESCRIPTION OF THE FIGURES

FIG. 1: Schematic Representation of the Expression Plasmids

FIG. 1 shows a schematic representation of the structure and production of the NPF-forming proteins described in the examples.

Figure 2:
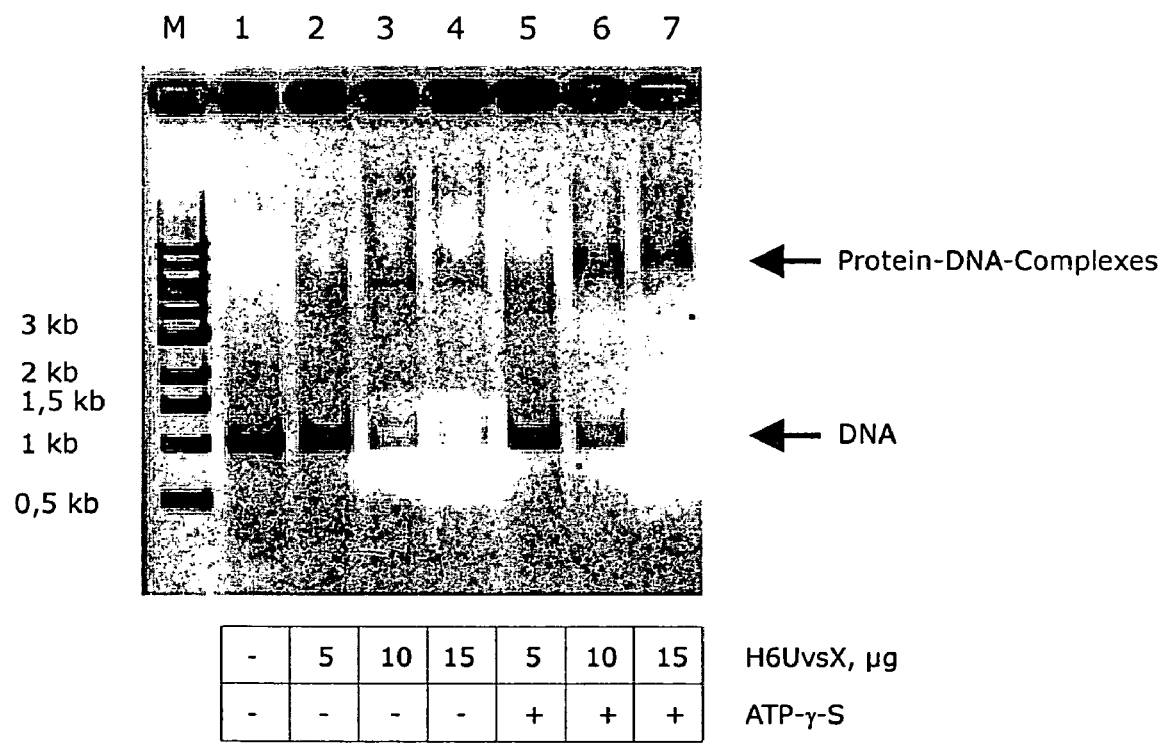

FIG. 2: Binding of UvsX to Double-Stranded DNA

FIG. 2 shows reaction mixtures of 200 ng (in each case) of a purified 1 kb PCR fragment with the given quantities of H6UvsX in 76 mM $K_2HPO_4$, 17 mM $KH_2PO_4$, 14 mM $NaH_2PO_4$, pH=7.2, 5 mM $MgCl_2$ and 0 or 1 mM ATP-γ-S, which was incubated in a final volume of 15 µl for 30 min at room temperature and then applied to a 0.8% TAE/agarose gel, which was afterwards stained with ethidium bromide.

Figure 3:
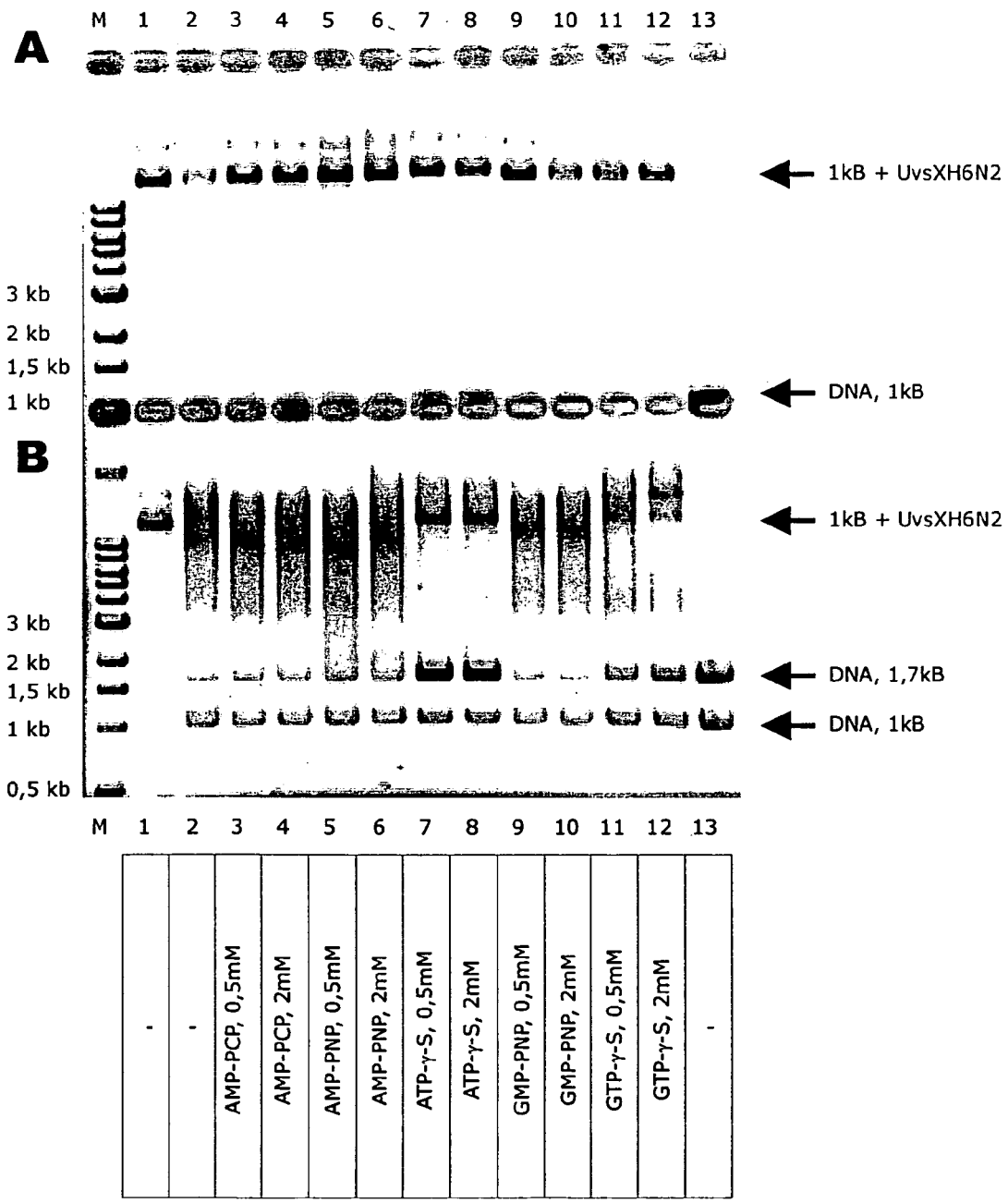

FIG. 3: Binding of NLS-modified UvsX to double-stranded DNA in the presence of different ATP analogues 250 ng of a purified 1 kb PCR fragment were incubated with 15 µg UvsXH6N2 in 76 mM $K_2HPO4$, 17 mM $KH_2PO_4$, 14 mM $NaH_2PO_4$, pH=7.2, 5 mM $MgCl_2$ and 0.5 or 2 mM of the given nucleotide analogue in a final volume of 20 µl for 30 min at room temperature. The reaction mixture was then split and 220 ng of a 1.7 kb PCR fragment was added to one half (B), incubated for a further 30 min at room temperature; all reaction mixtures were then applied to a 0.8% TAE/agarose gel, which was afterwards stained with ethidium bromide.

Figure 4:
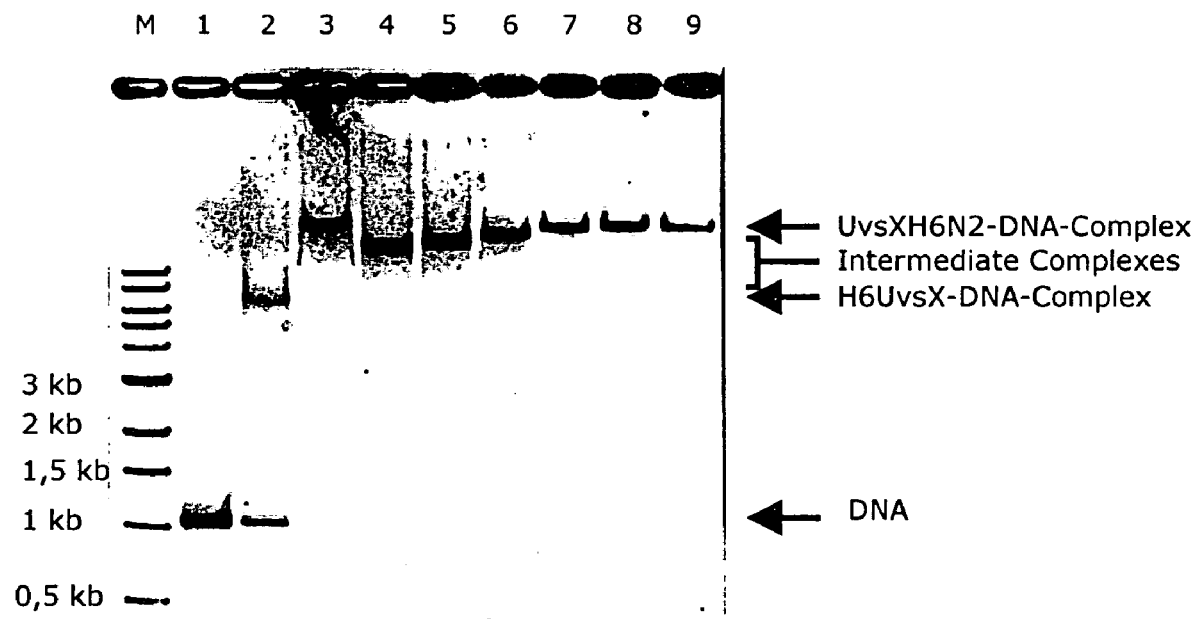

FIG. 4: Binding of a mixture of UvsX and modified UvsX to double-stranded DNA 200 ng (in each case) of a purified 1 kb PCR fragment was incubated in 76 mM $K_2HPO_4$, 17 mM $KH_2PO_4$, 14 mM $NaH_2PO_4$, pH=7.2, 5 mM $MgCl_2$ and 1 mM ATP-γ-S with the given quantities of purified H6UvsX or UvsXH6N2 for 30 min at RT and then all reaction mixtures were applied to a 0.8% TAE/agarose gel, which was afterwards stained with ethidium bromide. To exclude the possibility that the electrophoretic behavior of DNA is artificial as a result of salt, traces of imidazole or glycerine, samples of elution or dialysis buffer were included in tracks 8 and 9. (Final concentration: 1/10 vol elution buffer with 500 mM imidazole, 3/20 volumes dialysis buffer with 50% glycerine).

Figure 5:
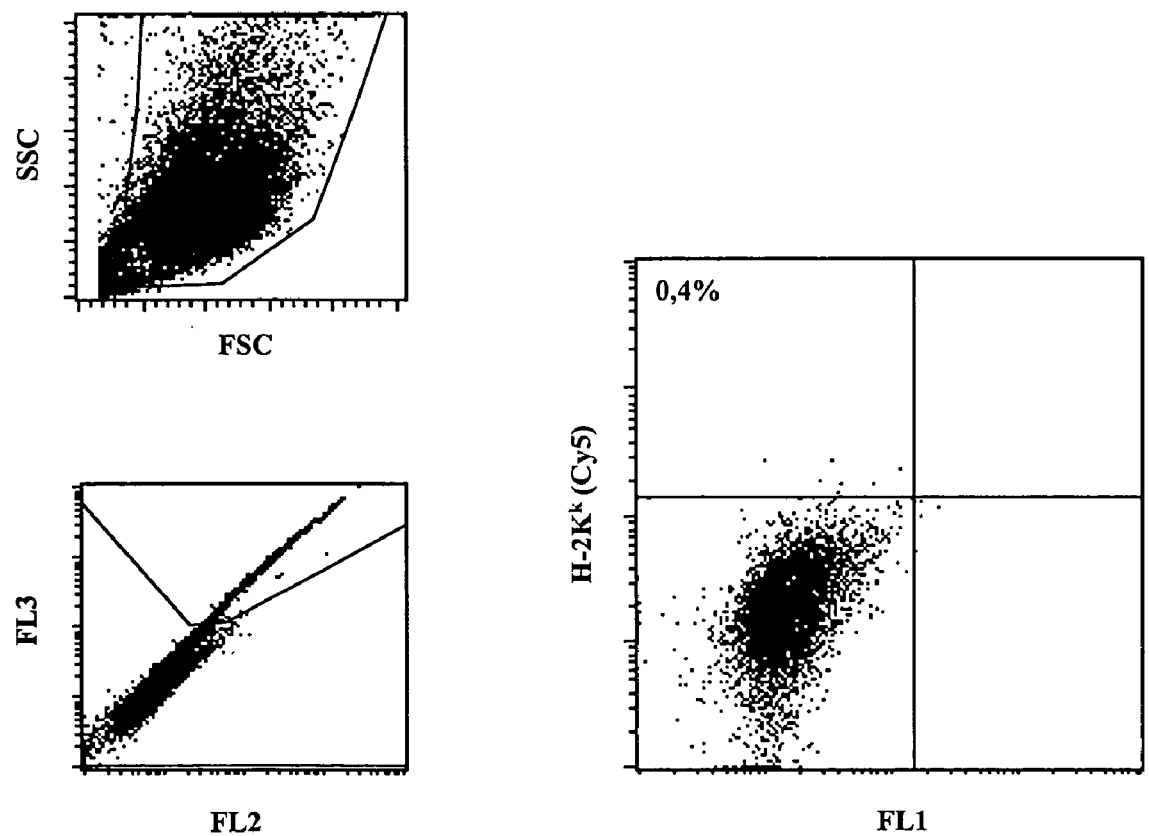
Figure 5:
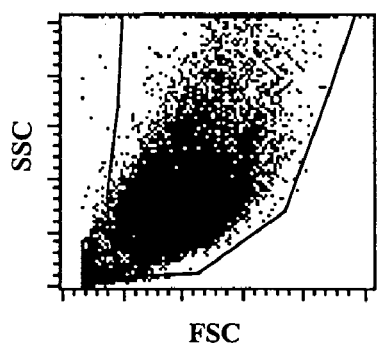
Figure 5:
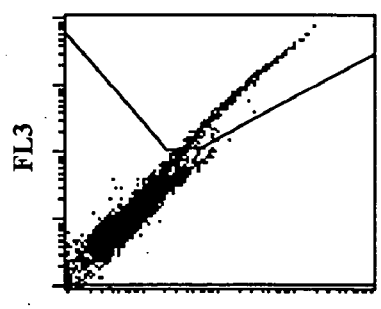
Figure 5:
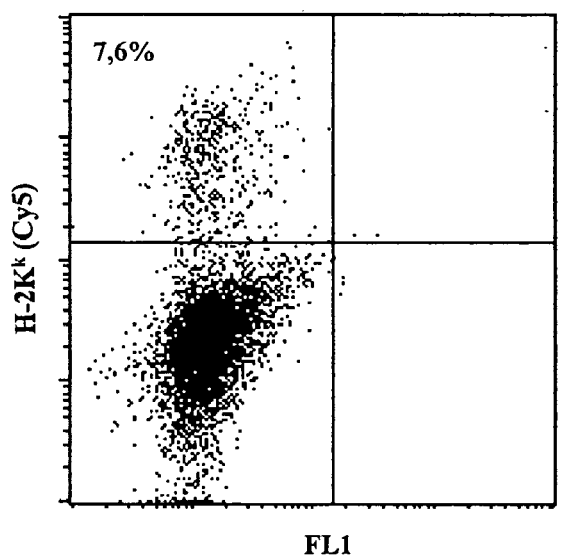
Figure 5:
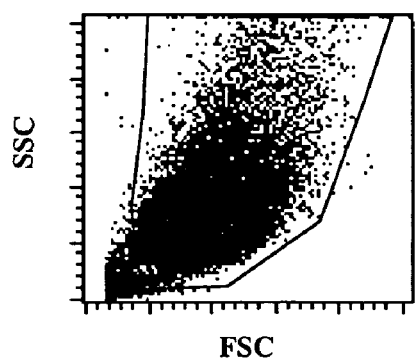
Figure 5:
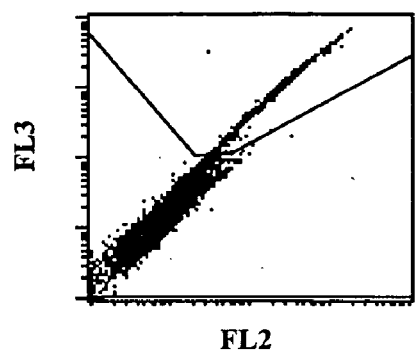
Figure 5:
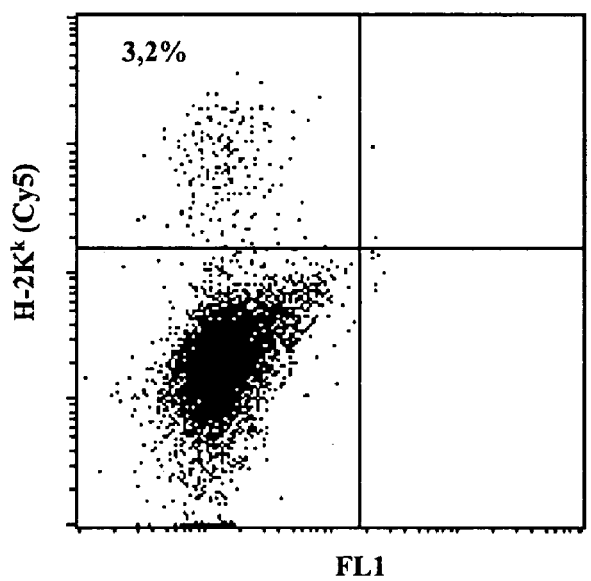
Figure 5:
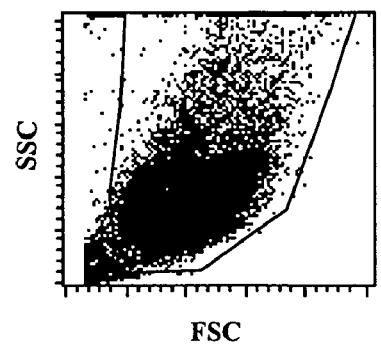
Figure 5:
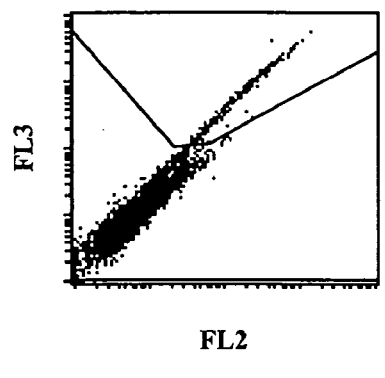
Figure 5:
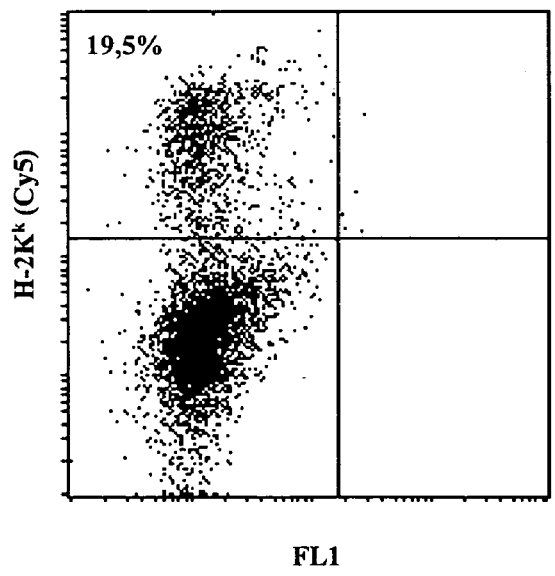
Figure 6:
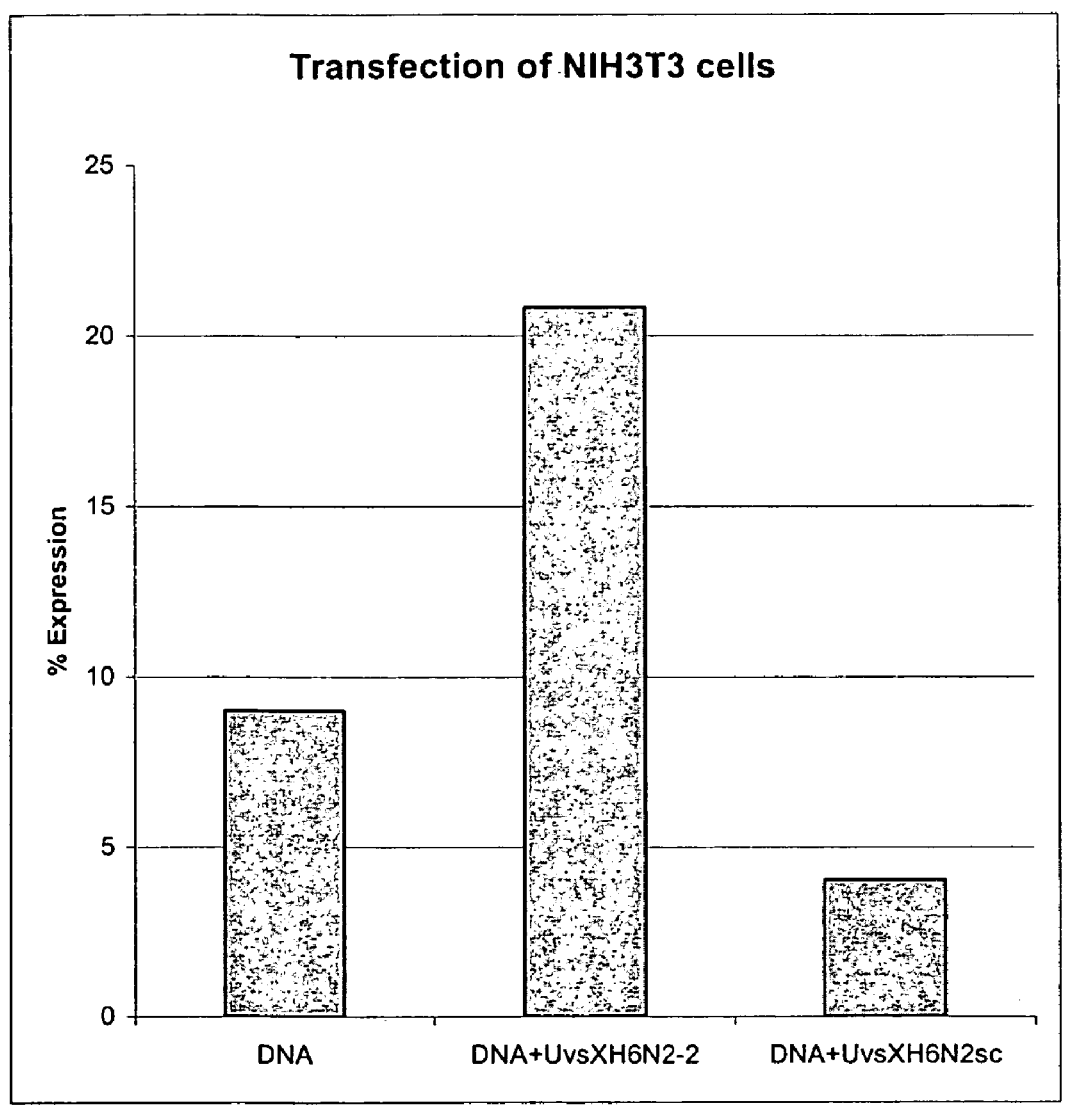

FIG. 5: FACScan Analysis of the Transfection of NIH3T3 Cells in Combination with Electroporation FIG. 5a-d shows an FACScan analysis: 5a) electroporation without DNA, 5b) electroporation of vector DNA without UvsX, 5c) with vector DNA packaged in UvsX, 5d) with vector DNA packaged in UvsX-NLS FIG. 6: A Further FACScan Analysis of the Transfection of NIH3T3 Cells in Combination with Electroporation FIG. 6 shows a bar diagram of the results of an FACSscan analysis of transfection with vector DNA packaged in UvsX-NLS (UvsXH6N2-2) and vector DNA packaged in UvsX "scrambled" NLS (UvsXH6N2sc).

Figure 7:
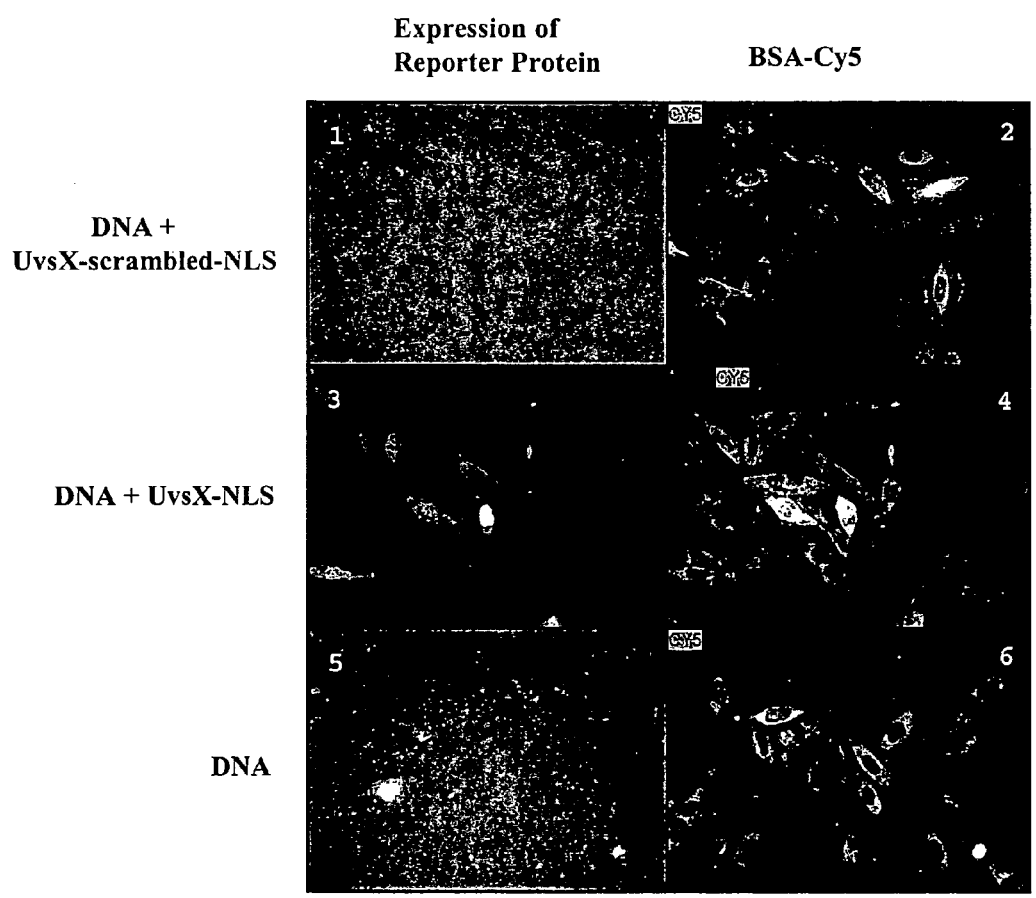

FIG. 7: Fluorescence Microscopic Analysis of the Transfection of NIH3T3 Cells in Combination with Microinjection.

The expression of a fluorescent marker protein (left side) is shown in microinjected NIH3T3 cells. BSA-Cy5 serves as injection marker, which is visualized in the corresponding fluorescence filter (right side). Pictures 1 and 2 show cells which were injected with DNA and UvsXH6N2sc in the cytoplasm; Pictures 3 and 4 show cells which were injected with DNA and UvsXH6N2-2; Pictures 5 and 6 show cells that were only injected with DNA.

Figure 8:
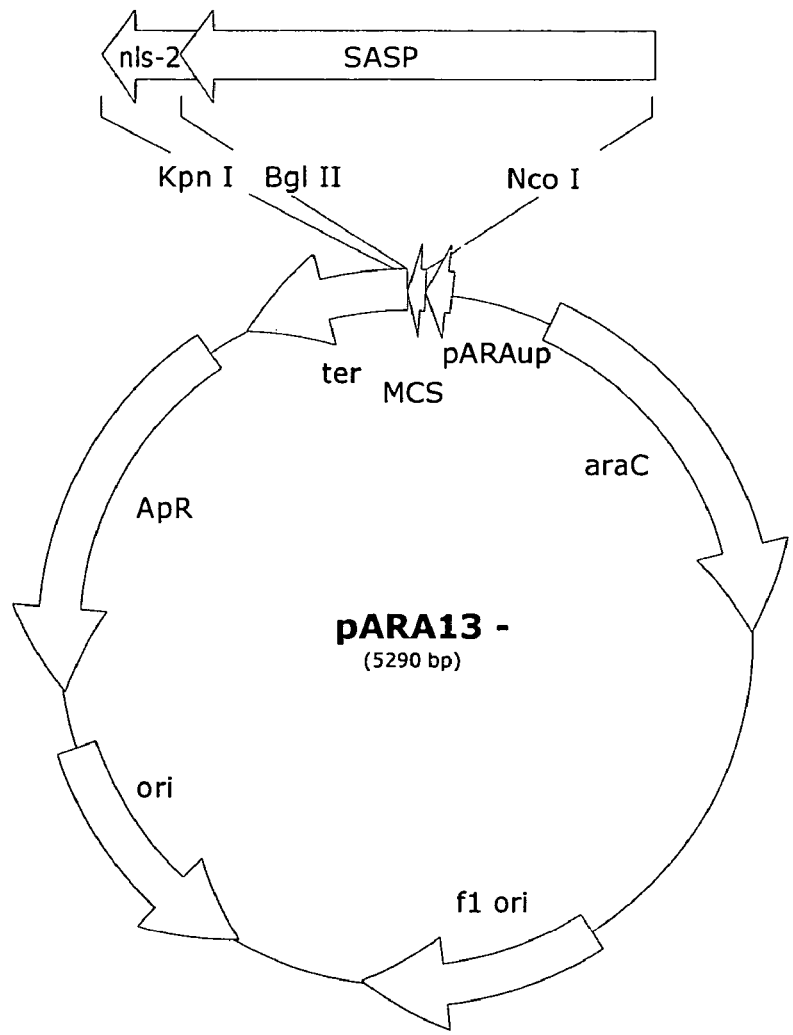

FIG. 8: Schematic Representation of the Expression Plasmids for SASP Proteins

FIG. 8 shows a schematic representation of the structure and production of the SASP proteins described in Examples 7 and 8.

Figure 9:
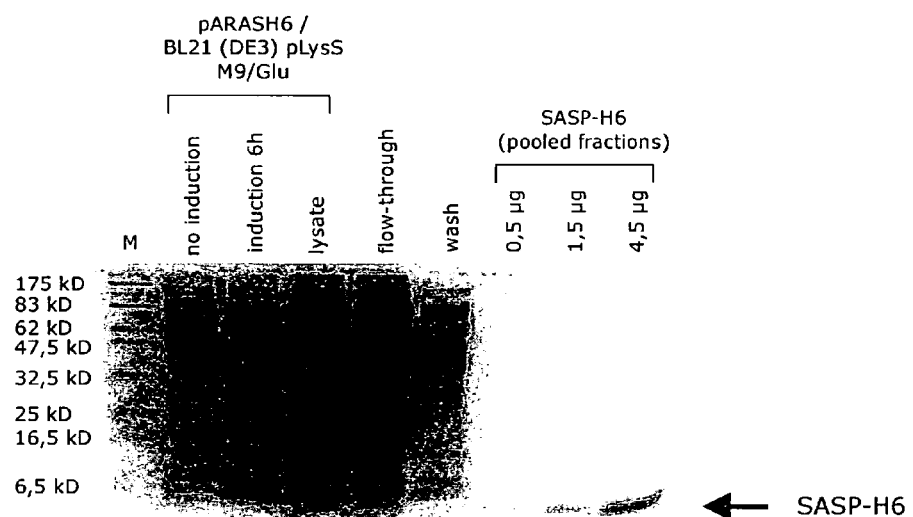
Figure 9:
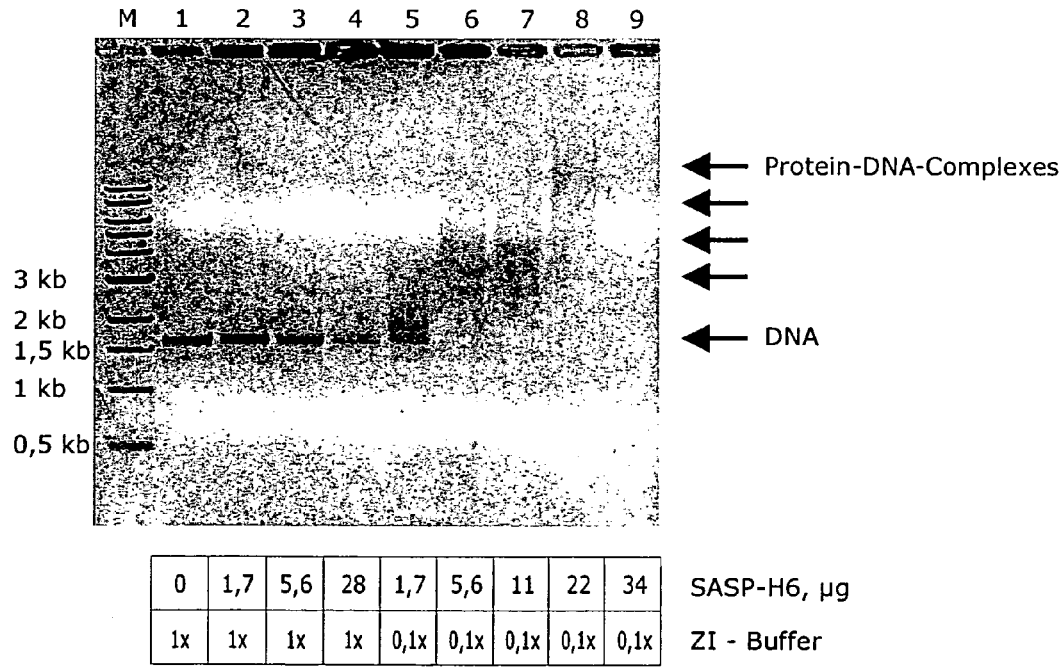

FIG. 9: (A) Purification of SASP Protein
(B) DNA Binding Ability of SASP Protein FIG. 9A shows an SDS gel with purified SASP protein. FIG. 9B shows the binding of DNA by SASP protein in a DNA shift analysis.

Figure 10:
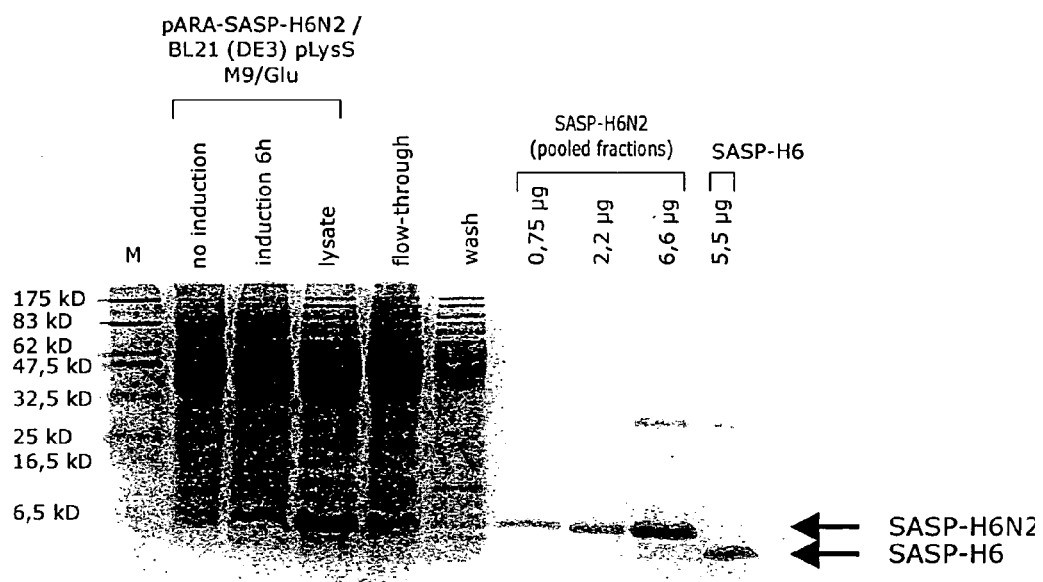
Figure 10:
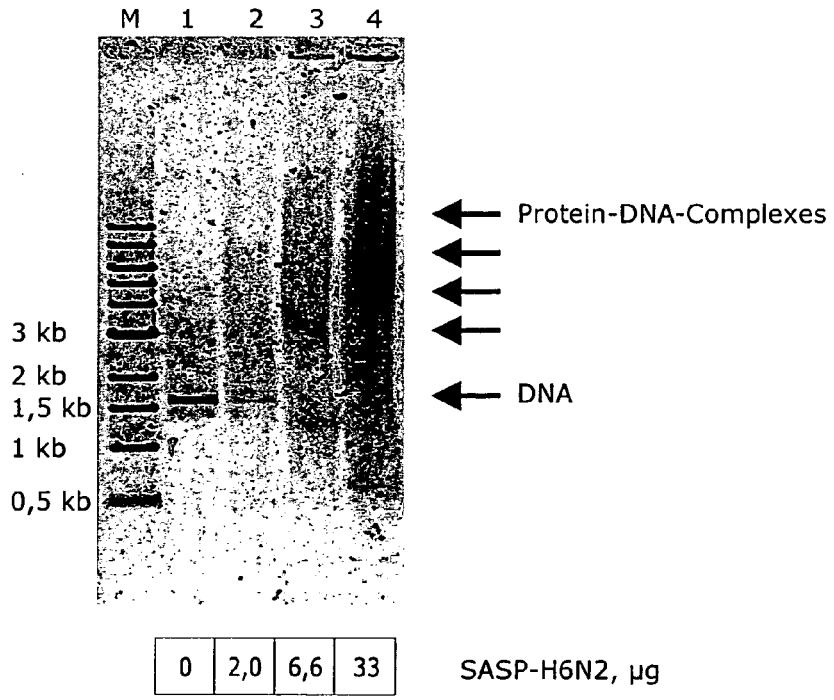

FIG. 10: (A) Purification of SASP-NLS-Protein
(B) DNA Binding Ability of SASP-NLS-Protein FIG. 10A shows an SDS gel with purified SASP-NLS-Protein (SASP-H6N2).

FIG. 10B shows the binding of DNA by SASP-NLS-Protein in a DNA shift analysis.

Figure 11:
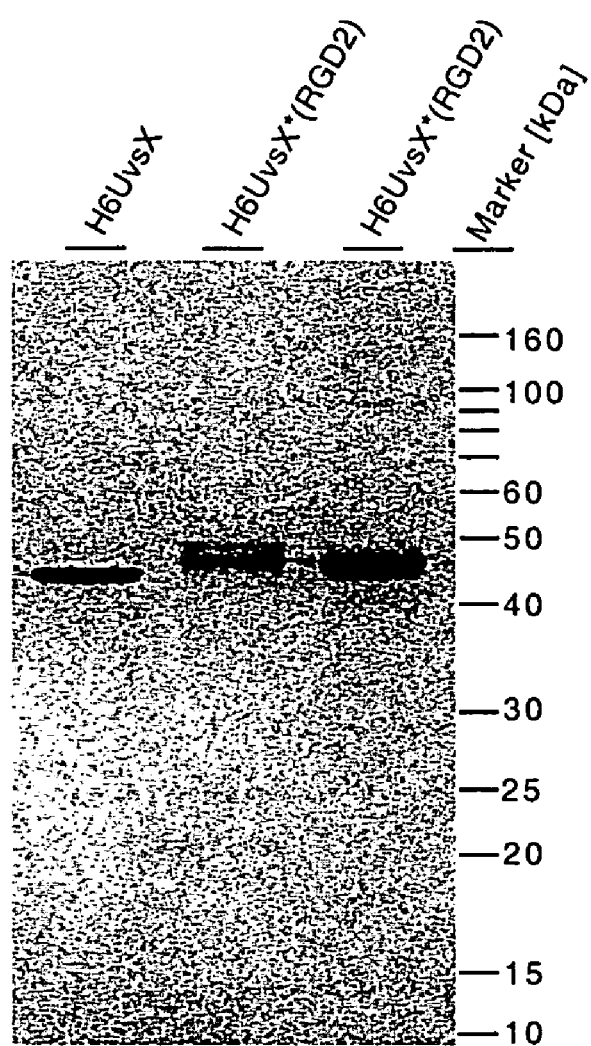

FIG. 11: Coupling of a Peptide with RGD-Motive to H6UvsX

FIG. 11 shows the electrophoretic separation of H6UvsX protein with and without the chemically coupled peptide RGD2. Two independently prepared samples of H6UvsX*(RGD2) are shown. 1 µg protein was applied in each track.

Figure 12:
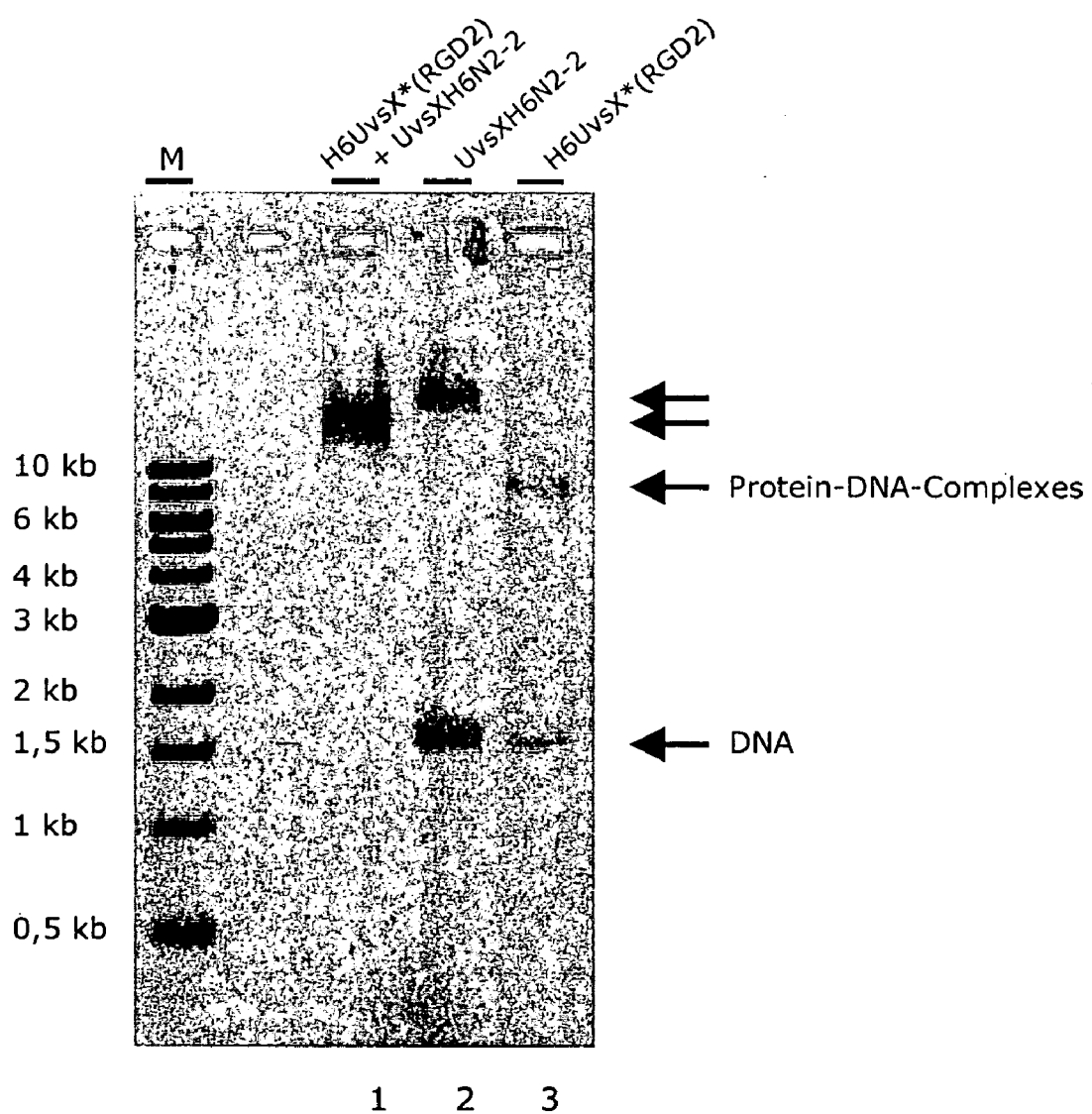

FIG. 12: Binding of Differently Modified UvsX Proteins to Double-Stranded DNA

FIG. 12 shows the separation in agarose gels of the NPFs consisting of a double-stranded DNA fragment and a mixture of H6UvsX*(RGD2) and UvsXH6N2-2 (Track 1), or of UvsXH6N2-2 alone (Track 2) or of H6UvsX*(RGD2) alone (Track 3).

Figure 13:
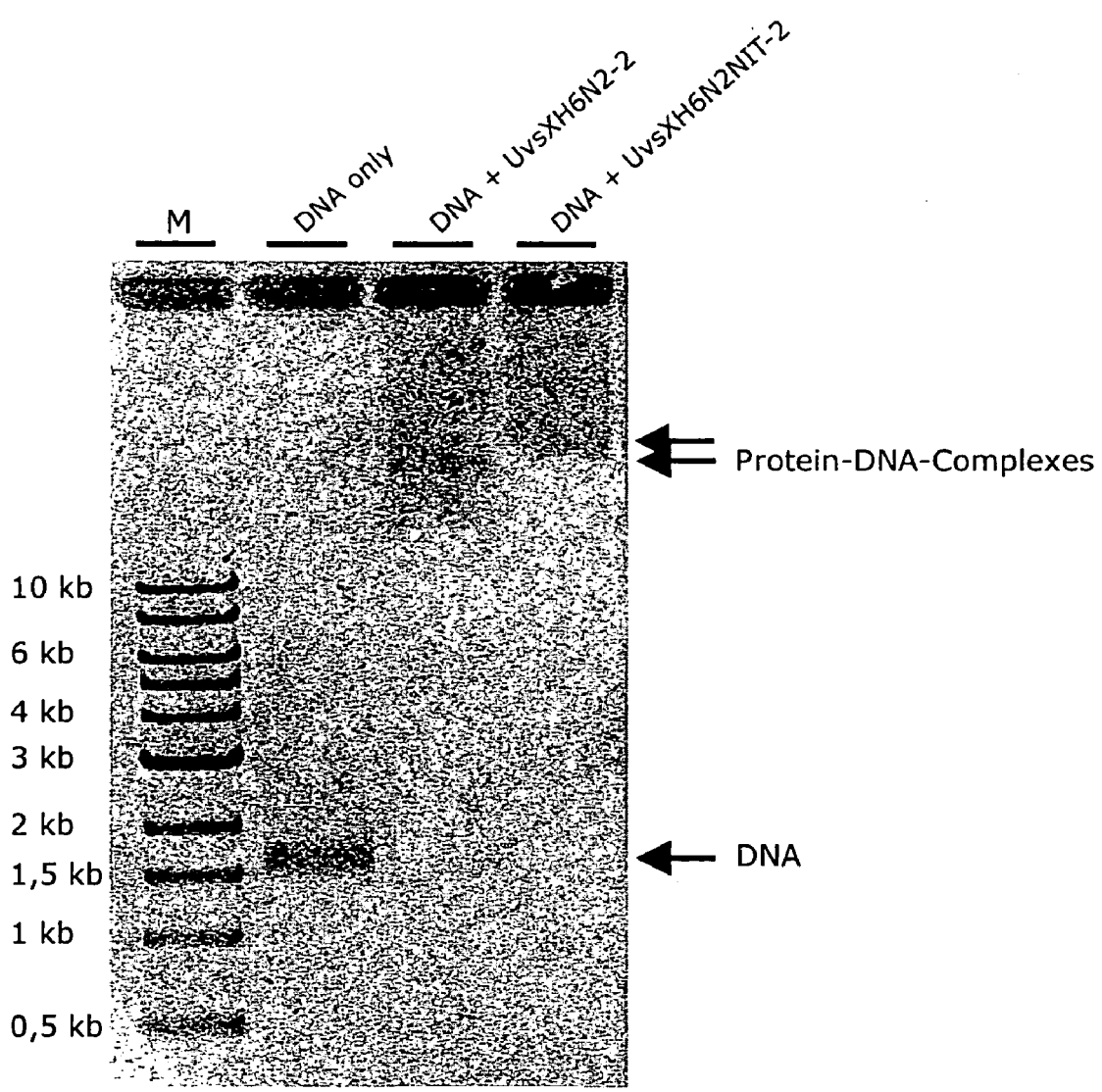

FIG. 13: DNA Shift Analysis of the Binding of UvsXH6N2 and UvsXH6N2NIT-2 to Fluorescein-Labeled DNA FIG. 13 shows a DNA shift of DNA-UvsXH6N2 and DNA-UvsXH6N2NIT-2. The proteins were incubated with a AlexaFluor488-labeled DNA fragment, as described in Example 10.

Figure 14:
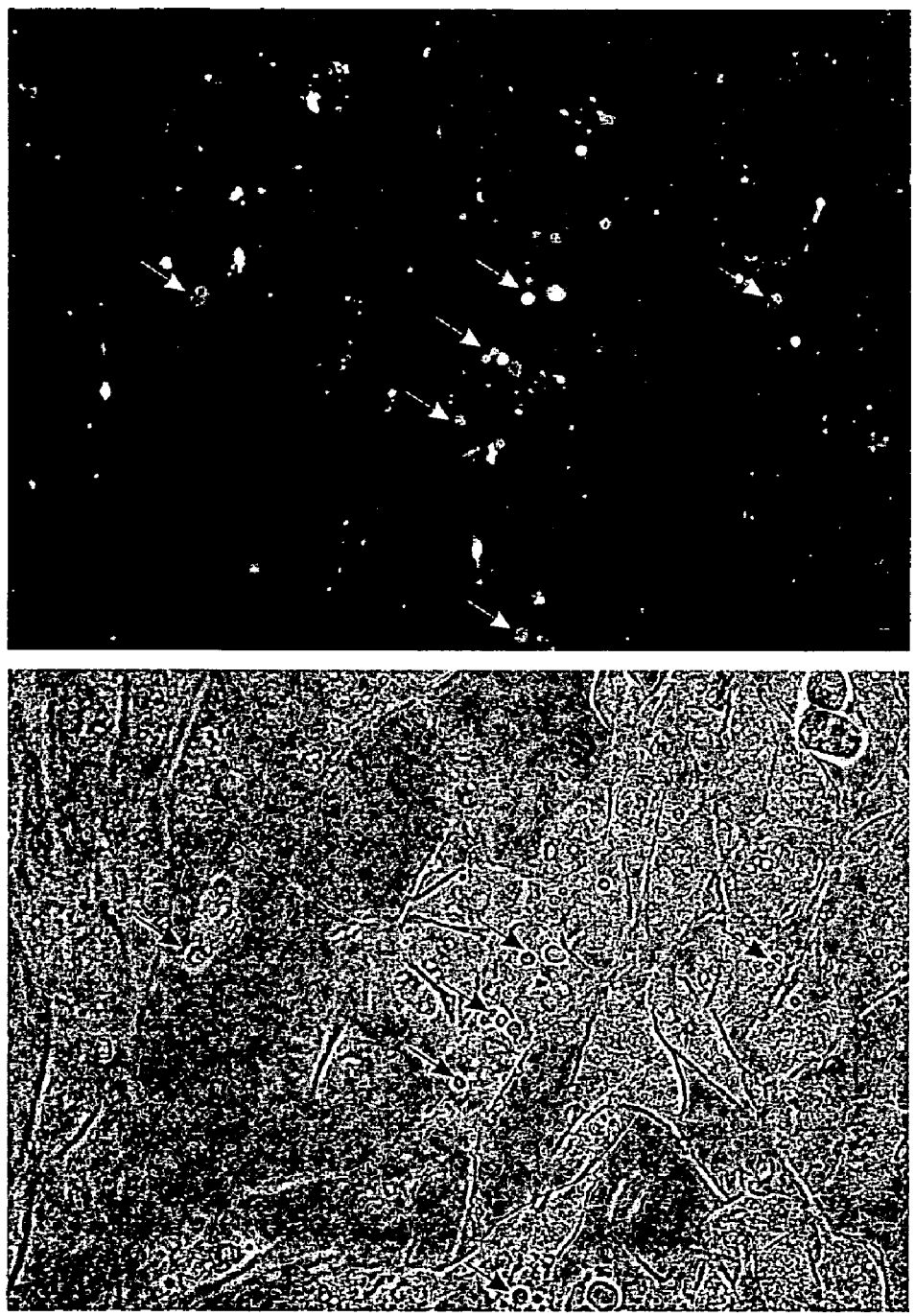
Figure 14:
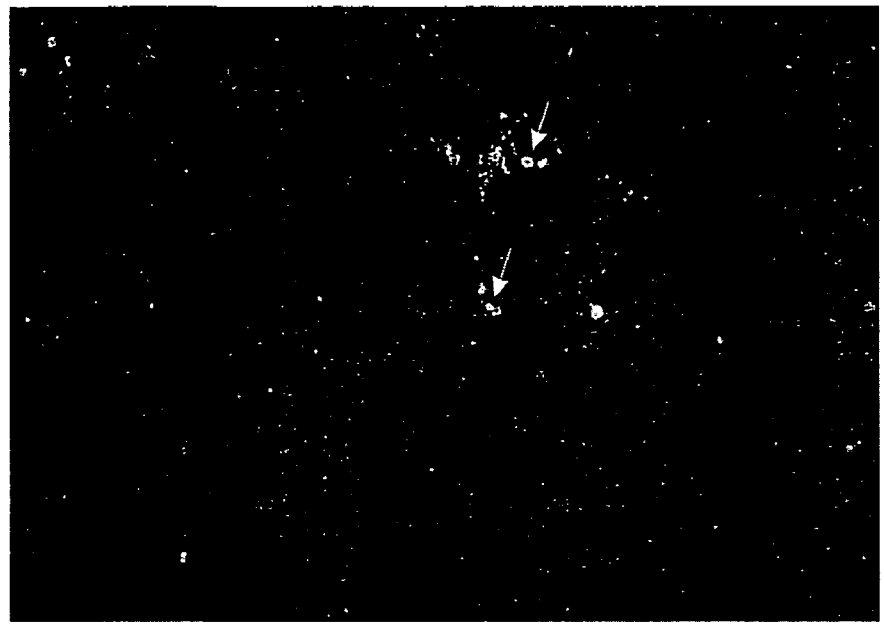
Figure 14:

FIG. 14: Fluorescence Microscopy Analysis of the Uptake of NPFs in NIH3T3 Cells by Endocytosis FIGS. 14a and 14b show fluorescence microscopy pictures of NIH3T3 cells. In each case, one picture shows a bright field image (bottom) and one in reflected light fluorescence (top). In the bright field, vesicular intracellular compartments are recognizable, which emit fluorescent light because of the endocytosed fluorescein-labeled DNA.

Figure 15:
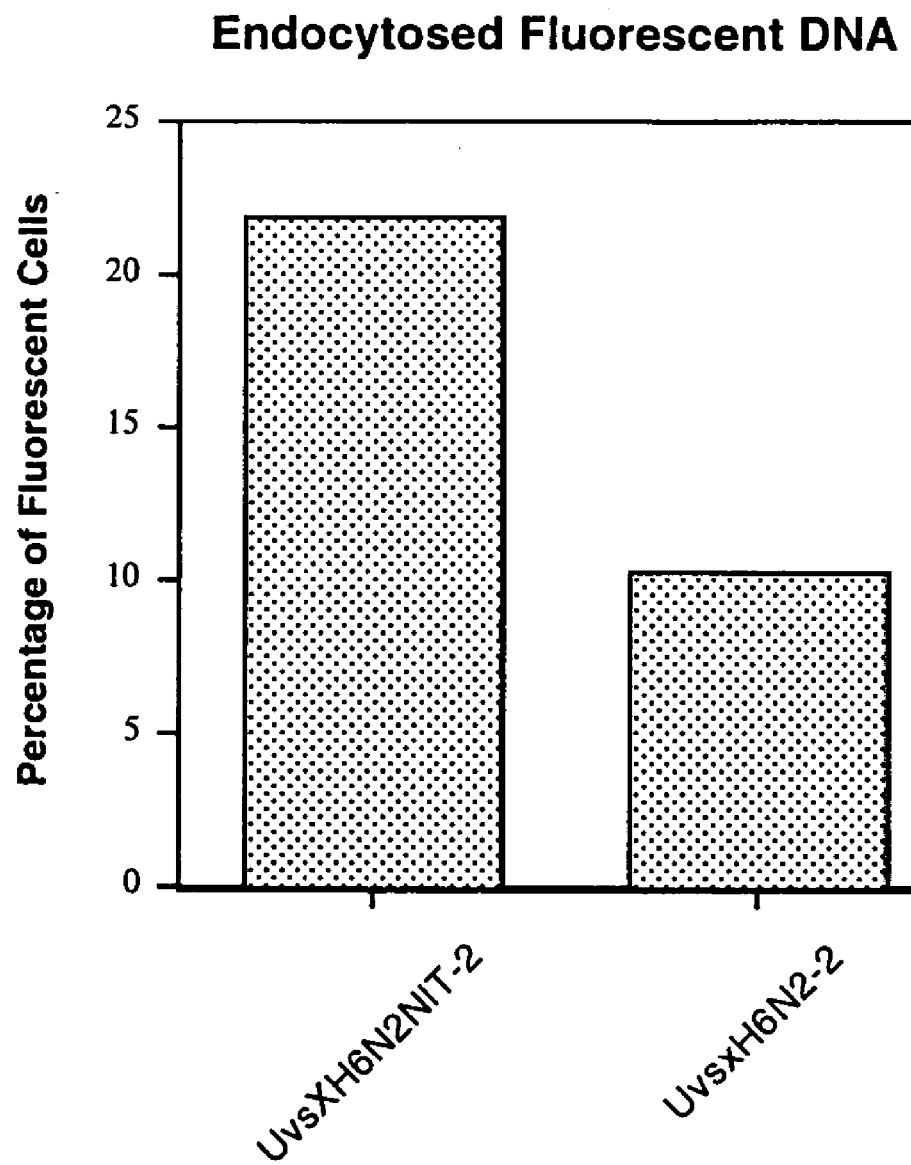

FIG. 15: Percentage of Cells with Endocytosed NPFs

FIG. 15 is a bar diagram which shows the percentage of the cells which inhibit at least one fluorescent vesicular compartment.

Figure 16:
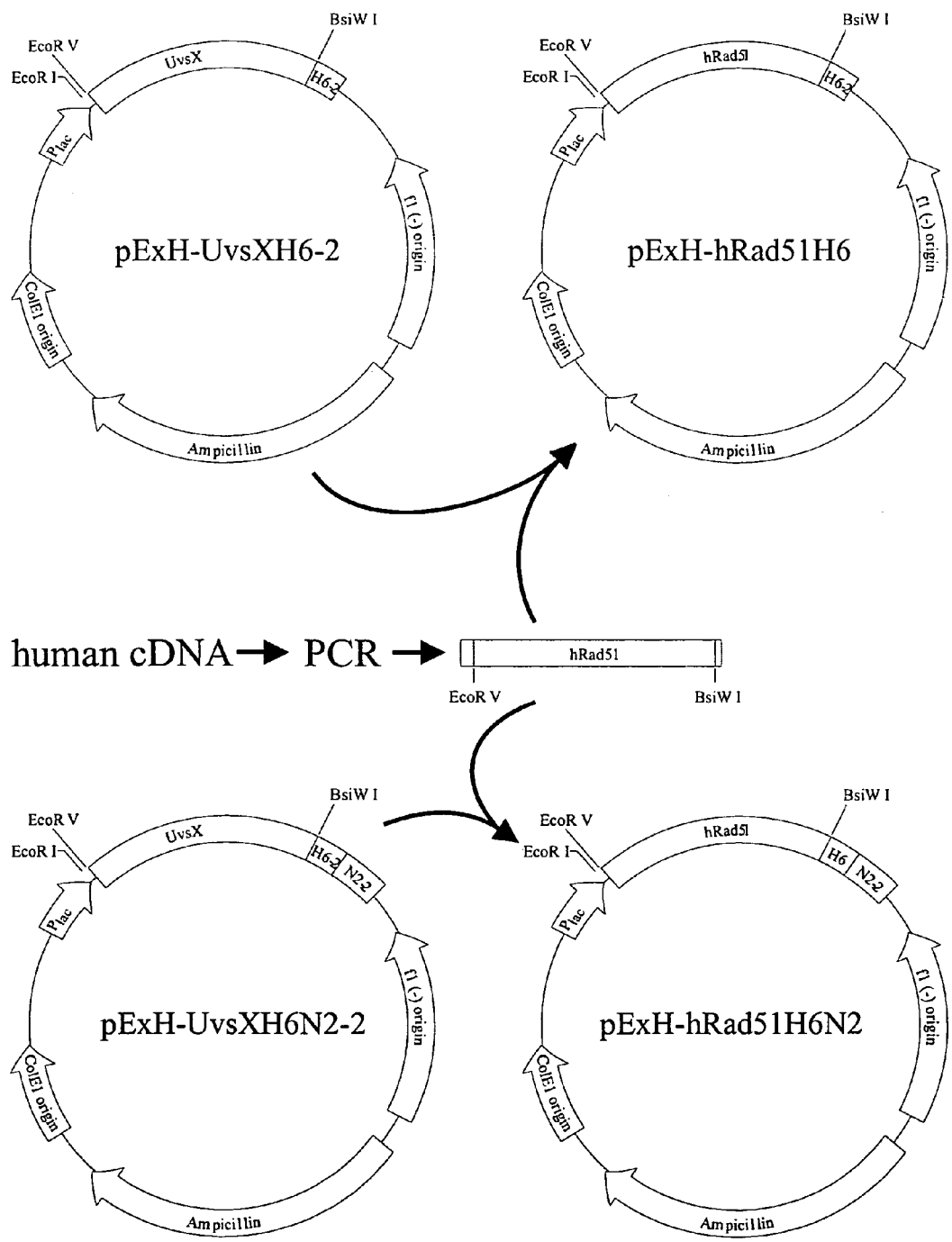

FIG. 16: Schematic Representation of the Expression Plasmids

FIG. 16 shows the schematic representation of the structure of the expression plasmids for the production of hRad51 fusion proteins.

Figure 17:
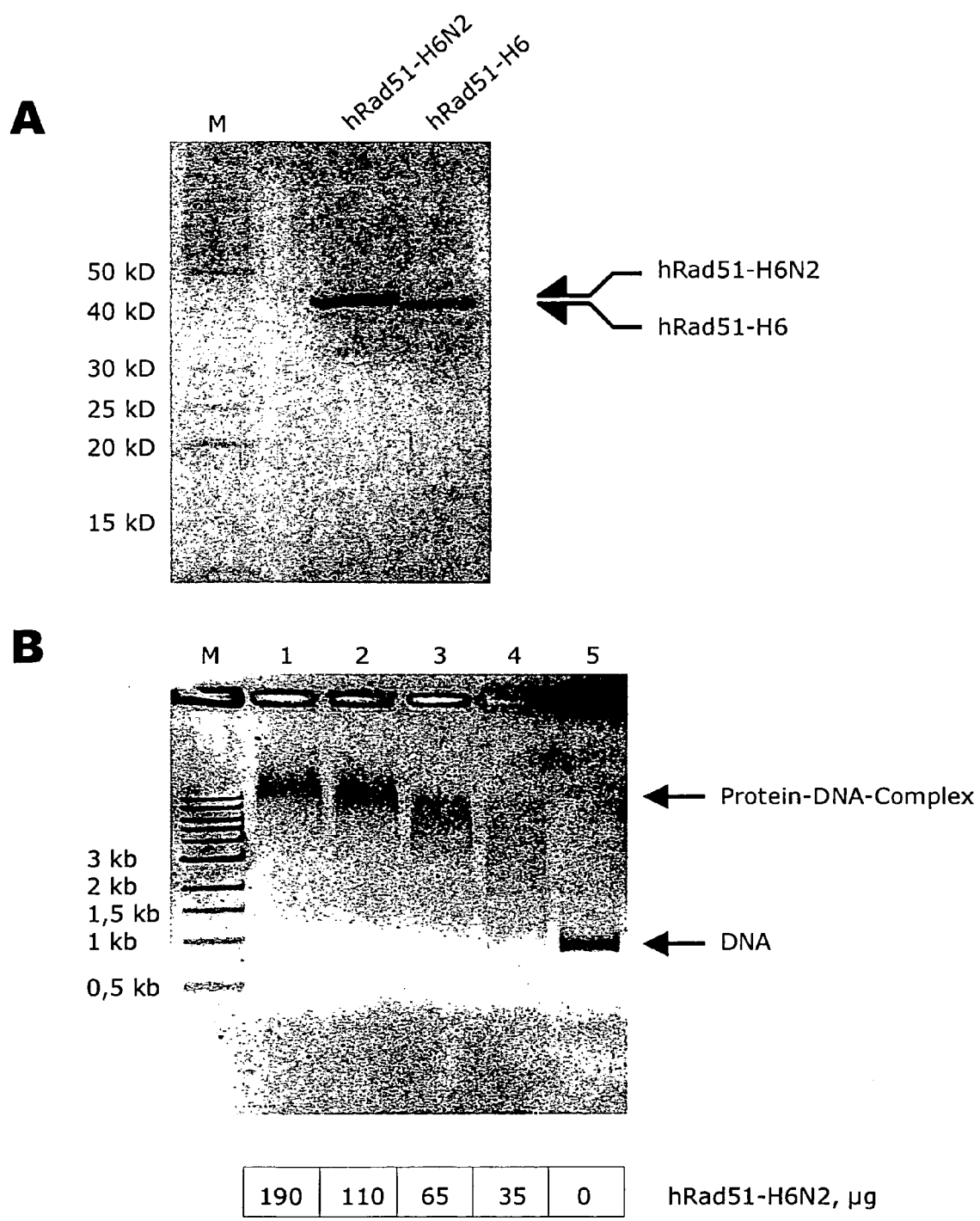

FIG. 17: Binding of NLS-Modified hRad51 (hRad51H6N2) to Double-Stranded DNA

FIG. 17(A) shows an SDS/Coomassie gel with hRad51H6N2 (12.7 µg) and hRad51 H6 (11 µg) after purification over nickel-chelate affinity chromatography. FIG. 17(B) shows reaction mixtures of 100 ng (in each case) of a purified 0.9 kb PCR fragment with the given quantities of hRad51H6N2 in 38 mM $K_2HPO_4$, 8.5 mM $KH_2PO_4$, 7 mM $NaH_2PO_4$, pH=7.2, 15 mM $MgCl_2$, 2.5 mM ATP and 25% glycerine, which were incubated in a final volume of 30 µl for 10 min at 37° C. and then applied to a 1% TAE/agarose gel which was afterwards stained with ethidium bromide.

Figure 18:
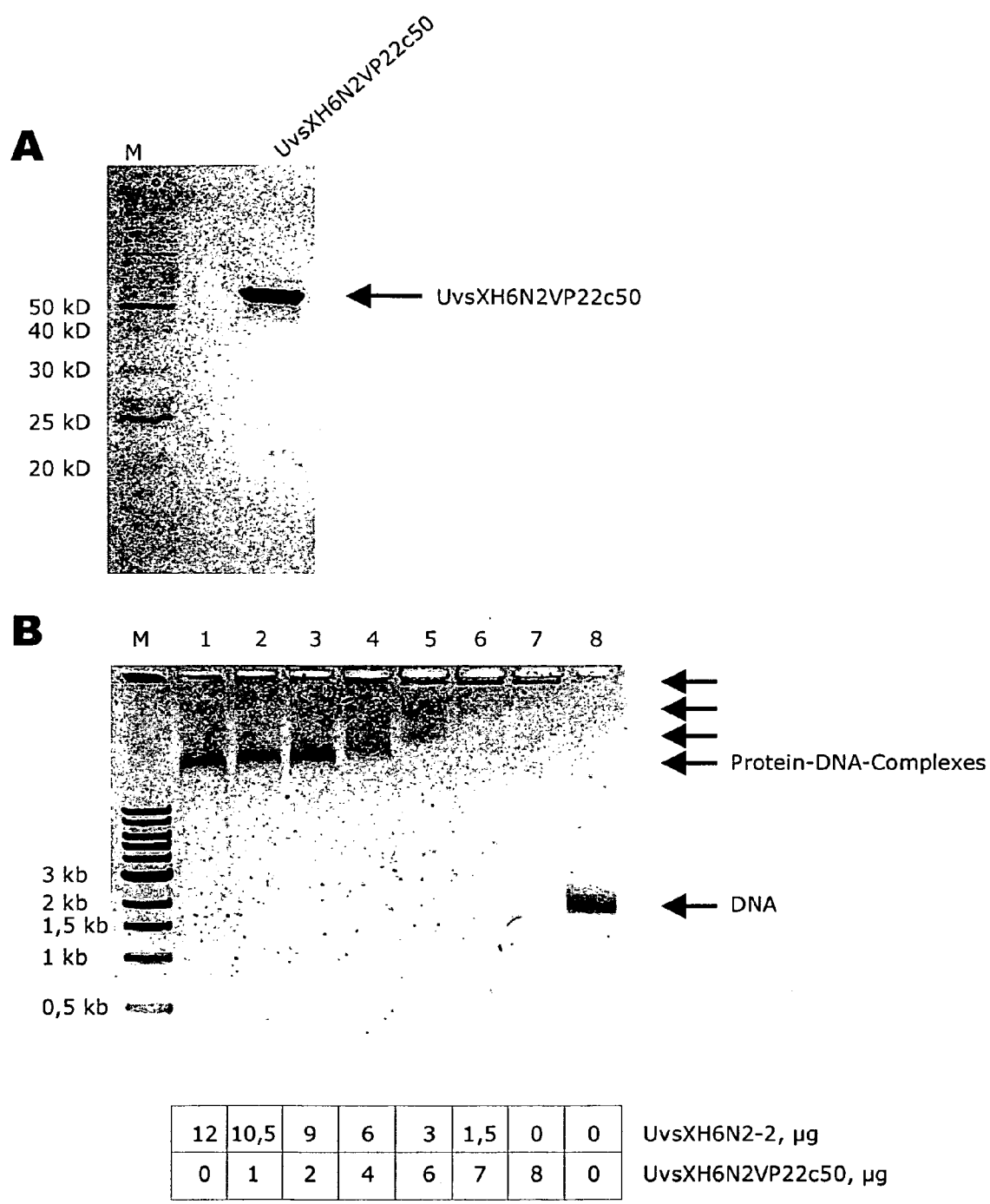

FIG. 18 Binding of a Mixture of Differently Modified UvsX (UvsX-NLS-VP22 and UvsX-NLS) to Double-Stranded DNA FIG. 18(A) shows a SDS/Coomassie gel with UvsXH6N2VP22c50.

FIG. 18(B): 140 ng (in each case) of a purified 1.7 kb PCR fragment were incubated in 96 mM $K_2HPO_4$, 21.5 mM $KH_2PO_4$, 18 mM $NaH_2PO_4$, pH=7.2, 5 mM $MgCl_2$ and 1.3 mM ATP-γ-S with the indicated quantities of purifed UvsXH6N2VP22c50 or UvsXH6N2-2 for 30 min at RT. All reaction mixtures were then applied to a 0.8% TAE/agarose gel, which was afterwards stained with ethidium bromide.

Figure 19:

FIG. 19: Transfected NIH3T3 Cells after Treatment with Complexes of DNA and a Mixture of UvsX-NLS-VP22 and UvsX-NLS Fluorescence microscopy picture of NIH3T3 cells, 24 h after treatment with complexes of 1 µg expression vector DNA and a mixture of 19 µg UvsXH6N2VP22c50 and 39 µg UvsXH6N2-2.

Figure 20:
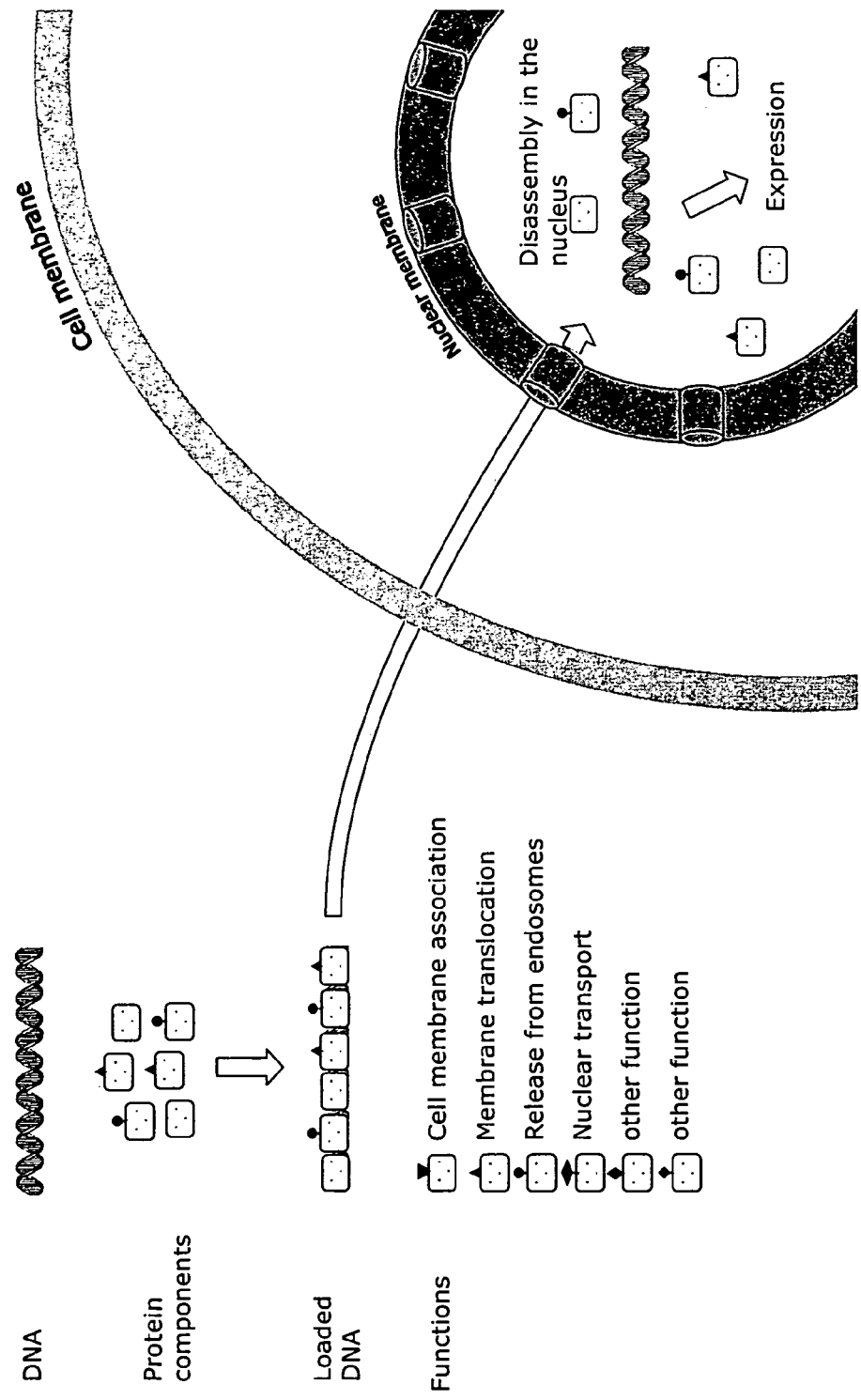

FIG. 20: Schematic Representation of the Basic Structure of the Method and Transfection Agent based on Nucleoprotein Filaments, according to the Invention.

DESCRIPTION OF THE INVENTION

The following examples are intended to describe the invention in detail, without limiting it to exemplary disclosed substances and methods.

EXAMPLE 1

Generation of Recombinant UvsX as NPF Forming Proteins

The proteins UvsXH6, UvsXH6-2, H6UvsX und H6UvsX-2 were used as NPF forming proteins (see FIG. 1).

Structure of the Proteins:

UvsXH6 (400 amino acids):

Amino acids 1-391: UvsX from the phage T4 (NCBI protein accession no: AAD42669, amino acids 1-391), amino acids 392-394: linker consisting of the amino acids $G^{392}GS^{394}$, amino acid 395-400: $H^{395}HHHHH^{400}$ for purification by nickel chelate affinity chromatography, amino acid exchange: $L^{43} \rightarrow P$.

UvsXH6-2 (403 amino acids):

Amino acids 1-391: UvsX from the phage T4 (NCBI protein accession no: AAD42669, amino acids 1-391), amino acids 392-394: linker consisting of the $S^{392}YG^{394}$, amino acids 395-400: $H^{395}HHHHH^{400}$, amino acids 401-403: C-terminus consisting of the amino acids $M^{401}YS^{403}$.

H6UvsX (404 amino acids):

Amino acids 1-4: N-terminus consisting of the amino acids $M^1SYS^4$, amino acids 5-10: $H^5HHHHH^{10}$, amino acids 11-13: linker consisting of the amino acids $S^{11}YG^{13}$, amino acids 14-404: UvsX from the phage T4 (NCBI protein accession no: AAD42669, amino acids 1-391), amino acid exchange: $Q^{340} \rightarrow L$.

H6UvsX-2 (404 amino acids):

Amino acids 1-4: N-terminus consisting of the amino acids $M^1GYS^4$, amino acids 5-10: $H^5HHHHH^{10}$, amino acids 11-13: linker consisting of the amino acids $S^{11}YG^{13}$, amino acids 14-404: UvsX from the phage T4 (NCBI protein accession no: AAD42669, amino acids 1-391).

Cloning of the Expression Plasmids

For the expression of the aforementioned proteins in suitable *Escherichia coli* cells, plasmids were constructed containing a coding sequence for UvsXH6, UvsXH6-2, H6UvsX or H6UvsX-2 under the control of the lac promotor (pExH-UvsXH6, pExH-UvsXH6-2, pExH-H6UvsX or pExJ-I-H6UvsX-2, see FIG. 1). The plasmids were generated by ligation of two PCR products. The first PCR product was amplified from pMCS5 (MoBiTec, Göttingen, Germany). pMCS5 is constructed in a similar way as pBluescript SK(–) (Stratagene) and is only different in the 5' region of the coding sequence of the lacZα fragment. PMCS5 therefore contains the lac promotor followed by the lac operator, by which the expression of an inserted coding sequence is based on the absence of active lac repressor. In order to achieve constitutive expression in any case, the amplification primers were selected in such way, that the lac operator is not present anymore in the PCR product. The resulting PCR product corresponded to pMCS5 from position 992 to 664 plus restriction overhangs. The nucleotides GAATTC (EcoRI restriction site) as well as TGTGTG were added before position 992 (3' to the lac promotor), and the nucleotides ACTAGT (Spe I restriction site) and CACACA were added behind position 664 to enable the ligation after digestion with the restrictions enzymes EcoRI and SpeI. The coding sequence for UvsXH6, UvsXH6-2 or H6UvsX and H6UvsX-2 was obtained by PCR amplification of T4 DNA using primers which contain the desired restriction sites, a ribosomal binding site and the additional codons. At their 5' end before the start codon, the PCR products contained the additional nucleotides 5'-CACACAGAATTCATAAAG-GAAGATATCAT-3' (SEQ ID NO:2), as well as the additional nucleotides 5'-ACTAGTTGTGTG-3' (SEQ ID NO:3) at their 3' end after the stop codon.

Purification:

An overnight culture of pExH-H6UvsX in DH5 was inoculated with 1.5-3l dYT/ampicillin (200 µg/ml) 1:1000, and was grown over night at 37° C. with 250 UPM. The cultures were harvested at 7000×g, and yielded approx. 5-15 g bacteria sediment. This was frozen for 1-3 days at −20° C. The sediment was thawed on ice and resuspended in 10-20 ml cold starting buffer. The lysis was carried out under slow stirring for 1 h at 4° C. using 10 ml lysozym (Serva, 190.000 u/mg) and approx. 4 g glass beads (Sigma, G-8893). Then, 50 µl DNAse I (Serva, 2 mg/ml) were added and further incubated for another 30 min. After centrifugation of the lysate (45 min, 11.000×g, 4° C.), the supernatant was filtered through a sterile filter (pore size 0.45 µm) and loaded on an equilibrated 1 ml HiTrap™ Chelating column (Pharmacia) preloaded with $Ni^{++}$ ions. The further purification steps were carried out according to the respective Pharmacia protocol for proteins containing a histidin hexamer. Aliquots of the various elution fractions were added to SDS/Coomassie gels. The purest fractions were combined and further concentrated in Centriplus YM30 columns (Millipore) according to the respective protocol. Then, it was dialyzed twice (dialysis tube: Spectra/Por, MWCO: 25.000) against an at least one thousand-fold volume of ZI buffer for at least one hour at 4° C., then over night at 4° C. against ZI buffer/50% glycerine. The dialysate was aliquoted in 30-50 µl fractions and stored at −80° C.

Used Buffers:

ZI buffer: 76 mM $K_2HPO_4$, 17 mM $KH_2PO_4$, 14 mM $NaH_2PO_4$, pH=7.2

Starting buffer: 20 mM Pi, 0.5 M NaCl, 10 mM imidazole, pH=7.4

Washing buffer: 20 mM Pi, 0.5 M NaCl, 20-50 mM imidazole, pH=7.4

Elution buffer: 20 mM Pi, 0.5 M NaCl, 100-500 mM imidazole, pH=7.4

Determination of Concentration:

The concentration of the UvsX proteins was determined by measuring the $OD_{280}$ using the extinction coefficient calculated with the Gene Inspector™ (Textco, Inc.) software. For H6UvsX it was 2.5-3.5 µg/µl.

Description of the Experiment:

H6UvsX, purified over $Ni^{++}$ sepharose, was incubated with 200 ng of a 1 kb PCR fragment (with and without 1 mM ATP-γ-S).

A shift of the DNA in the agarose gel caused by protein binding shows, that H6UvsX binds double-stranded DNA based on the concentration, and that this binding is enhanced by ATP-γ-S.

With ATP-γ-S, protein-DNA complexes are formed which can be stained more intensely with ethidium bromide than without ATP-γ-S, which indicates a topological change of the nucleoprotein filament by the nucleotide analog.

EXAMPLE 2

Generation of a Transfecting Agent, Based on UvsX as NPF Forming Protein With a Nuclear Localization Signal as a Functional Component.

As in example 1, plasmids were generated which permit the expression of the fusion proteins UvsXH6N2, UvsXH6N2-2, N2H6UvsX and N2H6UvsX-2, which are based on the proteins described in example 1, and in addition contain a nuclear localization signal (see FIG. 1).

Structure of the Proteins:

UvsXH6N2 (426 amino acids):

Amino acids 1-391: UvsX from the phage T4 (NCBI protein accession no.: AAD42669, amino acids 1-391), amino acids 392-394: linker consisting of the amino acids $G^{392}G\,S^{394}$, amino acids 395-400: $H^{395}HHHHH^{400}$, amino acids 401-403: linker consisting of the amino acids $G^{401}GS^{403}$, amino acids 404-417: nuclear localization signal nls-2 (amino acids 2-15, SEQ ID NO: 9 from WO 00/40742), amino acids 418-421: C-terminus of UvsX from the phage T4 (NCBI protein accession no: AAD42669, amino acids 388-391), amino acids 422-426: C-terminus consisting of the amino acids $K^{422}LVTG^{426}$, amino acid exchange: $Y^{238} \rightarrow V$.

UvsXH6N2-2 (420 Amino Acids):

Amino acids 1-391: UvsX from the phage T4 (NCBI protein accession no: AAD42669, amino acids 1-391), amino acids 392-394: linker consisting of the amino acids $S^{392}YG^{394}$, amino acids 395-400: $H^{395}HHHHH^{400}$, amino acids 401-403: linker consisting of the amino acids $M^{401}YS^{403}$, amino acids 404-417: nuclear localization signal nls-2 (amino acids 2-15, SEQ ID NO: 9 from WO 00/40742), amino acids 418-420: C-terminus consisting of the amino acids $G^{418}YP^{420}$.

N2H6UvsX (420 Amino Acids):

Amino acids 1-3: N-terminus consisting of the amino acids $M^{1}SY^{3}$, amino acids 4-17: nuclear localization signal nls-2 (amino acids 2-15, SEQ ID NO: 9 from WO 00/40742), amino acids 18-20: linker consisting of the amino acids $L^{18}YS^{20}$, amino acids 21-26: $H^{21}HHHHH^{26}$, amino acids 27-29: linker consisting of the amino acids $S^{27}YG^{29}$, amino acids 30-420: UvsX from the phage T4 (NCBI protein accession no: AAD42669, amino acids 1-391), amino acid exchange: $Q^{356} \rightarrow L$.

N2H6UvsX-2 (421 amino acids):

Amino acids 1-4: N-terminus consisting of the amino acids $M^{1}GYP^{4}$, amino acids 5-18: nuclear localization signal nls-2 (amino acids 2-15, SEQ ID NO: 9 from WO 00/40742), amino acids 19-21: linker consisting of the amino acids $S^{19}YS^{21}$, amino acids 22-27: $H^{22}HHHHH^{27}$, amino acids 28-30: linker consisting of the amino acids $S^{28}YG^{30}$, amino acids 31-421: UvsX from the phage T4 (NCBI protein accession no: AAD42669, amino acids 1-391).

Cloning of the Expression Plasmids:

For the expression in suitable *Escherichia coli* cells, plasmids were constructed containing a coding sequence for UvsXH6N2, UvsXH6N2-2, N2H6UvsX or N2H6UvsX-2 under the control of the lac promotor (pExH-UvsXH6N2, pExH-UvsXH6N2-2, pExH-N2H6UvsX or pExH-N2H6UvsX-2, see FIG. 1). The plasmids were generated as described in example 1 by ligation of two PCR products (see FIG. 1).

Purification:

The purification of UvsXH6N2 was carried out as described in example 1) for H6UvsX.

Concentration: 10-20 μg/μl.

Description of the Experiment:

UvsXH6N2 binds to double-stranded DNA. The binding is stabilized by ATP-γ-S: In order to examine the influence of various ATP analogues on the binding performance of UvsXH6N2 to DNA, the protein was first incubated with a 1 kb DNA fragment and various ATP analogues. Then, a 1.7 kb DNA fragment was added for competition. If the binding of the protein to the DNA is stabilized by addition of an ATP analog, it can be expected that UvsXH6N2 less likely binds a competing DNA fragment as long as no equilibrium is present. As can be seen in FIG. 3, the protein-DNA complex which was generated with the 1 kb fragment and UvsXH6N2, remains stable in absence of ATP-γ-S and the 1.7 kb fragment, compared to all other used ATP analogues, i.e. the 1.7 kb fragment apparently is not or only marginally occupied by liberated UvsXH6N2 molecules within the observation time.

EXAMPLE 3

Generation of a Transfection Agent With a Mixture of Modified and Unmodified NPF-Forming Protein Description of the Experiment:

Various ratios of H6UvsX and UvsxH6N2 were incubated with a 1 kb DNA fragment. The two proteins retarded the DNA in different degrees, due to their different molecular weight (see column 2 and 3 of FIG. 4). If the proteins are mixed before addition of DNA, intermediate complexes are formed based on the ratio of H6UvsX to UvsXH6N2, which yield a sharp band and therefore have an equal mean molecular weight. This shows that the DNA is statistically equally occupied by both proteins.

EXAMPLE 4

Transfection of a Cell Line (NIH3T3) With UvsX-NLS in Combination With Electroporation NIH3T3-Zellen (adherent, cultivated until 70-80% confluent) were transfected with a vector coding for the heavy chain of the murine MHC class I proteins H-2K$^K$. 1×10$^6$ cells were electroporated with 25 ng vector DNA which has been preincubated in binding buffer (76 mM $K_2HPO_4$, 17 mM $KH_2PO_4$, 14 mM $NaH_2PO_4$, 5 mM $MgCl_2$ pH 7.21) with 14 μg UvsX or UvsX-NLS as well as with or without 1 mM ATP-γ-S for 30 minutes at room temperature. For this, the cells were added to a total volume of 100 μl electroporation buffer (103 mM NaCl, 5.36 mM KCl, 0.41 mM $MgCl_2$, 23.8 mM $NaHCO_3$, 5.64 mM $Na_2HPO_4$, 11.2 mM glucose, 0.42 mM $Ca(NO_3)_2$, 20 mM HEPES, 3.25 μM gluthathione) and electroporated in a cuvette with 2 mm electrode spacing.

The electroporation was carried out by an exponential discharge at a voltage of 240 V and a capacity of 450 μF. The half-life of the voltage drop was typically 12 msec. Immediately after the electroporation, the cells were flushed out of the cuvettes with culture medium (RPMI with 10% FCS), incubated for 10 min at 37° C., and then transferred to a culture dish with prewarmed culture medium. After 6 h incubation, the cells were harvested and washed twice with PBS, and then incubated with a Cy5-coupled anti-H-2K$^K$ antibody and analyzed flow-cytometrically (FACScan). The number of dead cells was determined by staining with propidium iodine. Six hours after the electroporation, 7.4% or 8.7% of the cells transfected with free vector DNA express the H-2K$^K$ protein (minus the background of 0.25% in average). In comparison, the expression rate of the cells that have been transfected with vector UvsX was 2.9% or 3.8%. The expression rate after a transfection with vector UvsX-NLS was 19.2% or 18.9% (see FIGS. 5a-5d).

For examination of the nuclear transport, the physical procedure of electroporation was chosen so that no other biochemical components except UvsX influence the transfection. The tight binding of UvsX with ATP-γ-S to DNA, however, impairs the mobility of the complex in the electric field and therefore reduces the efficiency of the electroporation by approx. 60%. The attachment of a nuclear transport signal alone results in an increase of the expression shortly after the transfection by a factor of averagely 5.7 in this system. The increase of the expression rate by UvsX-NLS compared to UvsX therefore demonstrated that using a nuclear transport signal as functional component, DNA is transported into the nucleus by UvsX. An analysis performed shortly after the transfection is significantly improved since even cells become accessible that have not divided between transfection and analysis.

EXAMPLE 5

Transfection of a Cell Line (NIH3T3) With UvsX-Scrambled-NLS or UvsX-NLS in Combination With Electroporation Generation of UvsX-Scrambled-NLS In order to test the influence of the nuclear localization signal on the transfection, an UvsX derivative was generated for comparison purposes which corresponds in its net charge to an UvsX protein with a NLS, but itself does not contain a functional NLS.

Using partly homologous oligonucleotide primers, the UvsX gene was amplified from plasmid pExH-UvsXH6N2-2 (compare FIG. 1), so that the amino acid sequence SEQ ID NO:1 ("scrambled", i.e. a mixed NLS sequence) is expressed at the C-terminus of the resulting protein UvsXH6N2sc instead of the amino acid sequence EEDTPPKKKRKVED (SEQ ID NO:4("nls-", corresponding to the amino acids 2-15 from SEQ ID NO:9 from WO 00/40742). The scrambled amino acids correspond to the described nls-2 with respect to their composition but not with respect to their order. The net charges of UvsXH6N2-2 and UvsXH6N2sc are therefore equal, but only UvsXH6N2-2 contains an intact nuclear localization signal.

The protein UvsXH6N2sc was purified as described for the proteins in example 1.

NIH3T3 cells (adherent, cultivated until 70-80% confluent) were transfected with this vector coding for a fluorescent marker protein. For this purpose, 25 ng vector DNA in binding buffer (see example 1) were initially incubated with 1.5 mM ATP-γ-S and 16-18 μg of the described proteins for 30 min at room temperature. The protein-DNA complexes were each added to 3×10$^5$ NIH3T3-Zellen, resuspended in 80 μl electroporation buffer (140 mM Na$_2$HP$_4$/NaH$_2$PO$_4$, 10 mM MgCl$_2$, 5 mM KCl, pH 7.2). The electroporation was carried out in a cuvette with 2 mm electrode spacing by an exponential discharge at a voltage of 240 V and a capacity of 450 μF, The half life of the voltage drop was typically 12 msec. After addition of 400 μl medium, composed of RPMI 1640, Gibco company, 5% FCS, 2 mM glutamax (L-alanyl-L-glutamine, Invitrogen), 100 U/ml penicillin/streptomycin, 0.5 mM β-mercaptoethanol, the cells were added to culture dishes (6-well plates) with 1 ml prewarmed medium and were incubated at 37° C. and 5% CO$_2$. After 6 h, the flow-cytometric analysis was carried out (FACScan).

The result is graphically shown in FIG. 6: 9% of the cells transfected with free vector DNA express the marker protein. The expression rate of the cells that have been transfected with vector-UvsX-NLS (DNA+UvsXH6N2-2), however, was 21%. In comparison, the expression rate of the cells after transfection with vector-UvsX-scrambled-NLS (DNA+UvsXH6N2sc) was only 4%.

UvsX, modified with a nuclear localization signal therefore results in a markedly increased efficiency compared to free DNA and also compared to the modification by a non-functional nuclear localization signal. Since the latter transfection represents the control, this means that the transfection efficiency could be increased to 5-fold by modification of the UvsX. Therefore, the transfection efficiency can be markedly increased by the method according to the invention or the transfection agent. Furthermore a targeted control of the transfection method, here, for example, a directing into the nucleus, is possible in an advantageous way when the NPF-forming protein is modified (see also example 6).

EXAMPLE 6

Transfection of a Cell Line (NIH3T3) in Combination With Microinjektion 140 ng of a 1.7 kb expression vector DNA fragment were incubated with 9 μg modified UvsX protein as described above in binding buffer and 1 mM ATP-γ-S in a final volume of 20 μl for 30 min at RT. BSA-Cy5 was used as injection marker immediately before the injection in a concentration of approx. 1 μg/μl.

NIH3T3 cells that had been seeded to subconfluency the day before on CELLocate coverslips (Eppendorf) were microinjected through samples loaded onto Femtotipps (Eppendorf) using a micromanipulator and transjector (Eppendort) under an inverse fluorescence microscope (Leica DMIL).

The analysis was carried out in a fluorescence microscope (Olympus BX 60 fluorescence microscope, digital b/w camera SPOT-RT from Diagnostic Instruments Inc., analysis software: Metaview Imaging System from Universal Imaging Corporation) after 5 hours of further incubation of the cells at 37° C. and 5% CO2.

FIG. 7 shows microinjected NIH3T3 cells. The images 1 and 2 show cells that were injected with DNA and UvsXH6N2sc into the cytoplasm, the images 3 and 4 show cells that were injected with DNA and UvsXH6N2-2, and images 5 and 6 show cells that were injected only with DNA. Expression was only observed when the protein-DNA complexes contained UvsXH6N2-2, i.e. an UvsX protein modified with a nuclear localization signal (FIG. 7, image 3). In the cells of the controls (FIG. 7, image 5: only DNA, or FIG. 7, image 1: DNA with UvsX-scrambled-NLS) that had been clearly injected only in the cytoplasm and not in the nucleus during microinjection, no expression was observed, not even using a very long exposure.

EXAMPLE 7

Generation of Recombinant SASP as NPF-Forming Proteins

Cloning, Expression and Purification of the SASP Protein From B. subtilis

The SspC gene from *Bacillus subtilis*, which codes for a SASP („small acid-soluble spore protein"), was synthesized from 8 oligonucleotides according to the Khorana method (described in Bertram and Gassen: Gentechnische Methoden, Gustav Fischer Verlag, 1991, p. 212-213) and ligated between the NcoI and BgIII restriction sites of the plasmid pARA13 (Cagnon et al., 1991; Protein Engng. 4: 843-847). This was based on the protein sequence with the NCBI protein accession no: NP_389876. The reverse transcription to DNA was carried out using the codon preferences of genes, strongly expressed in *E. coli* and described in (Andersson and Kurland 1990; Microbiol. Rev. 54: 98-210). The resulting plasmid pARA13-SASP served as a matrix for the cloning of two other plasmids, which code for SASP proteins, carrying a polyhistidine sequence of 6 histidines either at the N-terminus (H6-SASP) or at the C-terminus (SASP-H6) (FIG. 8). The plasmids were transformed into the *E. coli* strain BL21 (DE3) pLysS (Novagen, Madison) and plated out on LB/ampicillin/glucose (0.2%).

20 ml M9 minimal medium (0.2% glucose) each was inoculated with single colonies and grown over night at 37° C. and 220 rpm. The following day, the cultures were induced with 0.2% arabinose at an $OD_{600}$ of approx. 1.0 and were grown for another 6 hours. Raw extracts (0.5 ml pelleted culture in PBS/loading buffer) were applied to high resolution SDS gels (according to Schagger and von Jagow 1987; Anal. Biochem. 166:368-79) and stained with Coomassie Blue (FIG. 9A). For preparative purification, 2 L M9/glucose were inoculated 1:200 with an overnight culture. Again, the culture was induced with 0.2% arabinose at an $OD_{600}$ of approx. 1,0, and further grown for 6 h. The bacteria were then pelleted and frozen at −20° C. In the following, the purification of SASP-H6 is described exemplary. Approx. 7 g of the pellet was thawed and resuspended in 14 ml starting buffer (see example 1), supplemented with a tablet of complete EDTA-free protease inhibitor cocktail, Roche, Mannheim, and sonificated on ice for 3 min at 280 Watts (Labsonic U, Braun Biotech, Melsungen repeating duty puls; 0.5 sec). The extract was centrifuged at 4° C. Apart from this, the purification was carried out as described for the UvsX proteins over HiTrap chelating columns (Amersham Pharmacia, Uppsala). The fractions between 200 mM and 500 mM imidazole, containing the protein in high concentration, were combined and concentrated to approx. 3 ml using centriplus columns (YM-3, Millipore, Eschborn). The SASP protein was then dialyzed three times against 1×ZI buffer (see example 1), and aliquots were frozen at −80° C. in a concentration of approx. 5 µg/µl.

Testing of the DNA-Binding Capacity of the SASP Protein 125 ng (in each case) of a 1.7 kb DNA fragment were preincubated with different amounts of SASP-H6 protein in 1×ZI buffer or ¹/₁₀×ZI buffer for 30 min at room temperature, and then applied to an 0.8% TAE-agarose gel. FIG. 9B shows that the DNA is completely bound by the protein. The diffuse appearance of the DNA-protein bands may be due to a dissociation of the proteins from the DNA during the gel run.

EXAMPLE 8

Generation of a Transfection Agent Based on SASP as NPF-Forming Protein With a Nuclear Localization Signal as Modification For generation of an SASP with a nuclear localization signal (NLS) as functional component, a DNA sequence coding for a nuclear localization signal („nls-2", amino acids 2-15, SEQ ID NO: 9 from WO 00/40742) was added to the C-terminus of the already available clone pARA13-SASP-H6 (see FIG. 8) by PCR amplification. The aforementioned plasmid served as PCR template. The resulting plasmid pARA13-SASP-H6N2 (see FIG. 8) was transformed as described in example 7, and the protein SASP-H6N2 was purified accordingly.

Testing of the Binding Ability of the SASP-NLS Protein 125 ng each of a 1.7 kb DNA fragment were preincubated with different amounts of SASP-H6N2 protein in 1×ZI-Puffer for 30 min at room temperature, and then applied to a 0.8% TAE-agarose gel.

FIG. 10B shows that the DNA is held back by the NLS-modified SASP as well. The DNA protein bands appear diffuse.

EXAMPLE 9

Generation of a Transfection Agent With a Integrin Binding Motif for the Association of the Complex to the Cell Surface as Functional Component Integrins are membrane-anchored adhesion proteins on the cell surface some of which recognize a peptide motif of three amino acids (arginine-glycine-aspartic acid or „RGD" motif) as binding partner. The binding results in clustering of several integrin molecules on the cell surface and in endocytosis (Plow et al., 2001). By modification of UvsX as NPF-binding protein with an RGD motif, it can be achieved that the transfection agens can be taken up specifically via integrins into the endosomal compartments of the cells.

Structure of the Proteins

The used proteins H6UvsX and UvsXH6N2-2 are identical to the ones shown in FIG. 1 and described in example 1 and 2.

The protein H6UvsX*(RGD2) was generated by chemical coupling. The protein named RGD2 is a nonapeptide (NI-TRGDTYI) consisting of the penton base protein of adenovirus type 7 (Bal et al., 2000), which has been synthesized in such way that a chemically active group is present at the N-terminal amino group (SMCC, succinimidyl 4[N-maleimidomethyl]-cyclohexane-1-carboxylat) which permits the coupling to free cysteine SH groups in the UvsX protein.

For the coupling, 6 nmol H6UvsX were incubated with 60 nmol peptide in 76 mM $K_2HPO_4$, 17 mM $KH_2PO_4$, 14 mM $NaH_2PO_4$, pH=7.2 for one hour at 37° C., and was then purified by several washing steps with incubation buffer over a MicroCon filter (10 kDa cut off) to remove excess peptide. The successful coupling was detected by an altered running performance in an SDS polyacrylamide gel electrophoresis. FIG. 11 shows two independently generated preparations of H6UvsX*(RGD2) on an SDS polyacrylamide gel. The coupled peptide results in an increase of the molecular weight and thus in an alteration of the running performance in SDS gels.

Description of the Experiment:

Binding of UvsX-NLS and UvsX-RGD to double-stranded DNA and formation of mixed NPFs:

Reactions with 140 ng (in each case) of a purified 1.6 kb PCR DNA fragment with a mixture of 15 µg H6UvsX*(RGD2) and 4 µg UvsXH6N2-2, with 4 µg UvsXH6N2-2 alone and with 15 µg H6UvsX*(RGD2) alone were incubated in 76 mM $K_2HPO_4$, 17 mM $KH_2PO_4$, 14 mM $NaH_2PO_4$, pH=7.2, 5 mM $MgCl_2$ and 1 mM ATP-γ-S in a final volume of 20 µl for 30 min at room temperature and were then transferred to a 0.8%

TAE/agarose gel which was afterwards stained with ethidium bromide. The electrophoresis was carried out at 100 V for 1 h.

FIG. 12 shows that the two differently modified proteins form NPFs with the DNA which markedly differ in their running performance. NPFs consisting of a double-stranded DNA fragment and a mixture of H6UvsX*(RGD2) and UvsXH6N2-2 (lane 1), or of UvsXH6N2-2 alone (lane 2) or of H6UvsX*(RGD2) alone (lane 3), were separated electrophoretically in an agarose gel. Since protein is present in low amounts, free DNA fragment is present as well. Both proteins in a reaction bind together to the DNA fragment and result in a mixed NPF that has a molecular weight that lies between that of the NPFs of the pure proteins (lane 1). From this it can be concluded that UvsX-NLS and UvsX-RGD bind to double-stranded DNA and can form mixed NPFs.

EXAMPLE 10

Specific Uptake of NPFs into Cells by Integrin-Mediated Endocytosis

Structure of the Proteins

As in example 1, plasmid UvsXH6N2NIT-2 (FIG. 1) which permits the expression of a fusion protein of UvsX and an integrin-binding RGD motif, was generated recombinantly.

Amino acids 1-391: UvsX from the phage T4 (NCBI protein accession no.: AAD42669, amino acids 1-391), amino acids 392-394: linker consisting of the amino acids $S^{392}YG^{394}$, amino acids 395-400: $H^{395}HHHHH^{400}$, amino acids 401-403: linker consisting of the amino acids $M^{401}YS^{403}$, amino acids 404-417: nuclear localization signal nls-2 (amino acids 2-15, SEQ ID NO: 9 from WO 00/40742), amino acids 418-420: C-terminus consisting of the amino acids $G^{418}YP^{420}$ and amino acids 421-432: RGD motif „NIT": $N^{421}ITRGDTYIPYP^{432}$ (SEQ NO:5).

Description of the Experiment:

Generation of NPFs from fluorescence-labeled DNA and UvsX derivatives:

1 µg each of a purified 1.6 kb PCR DNA fragment containing AlexaFluor488-labeled dUTP (Molecular Probes, Eugene, Oreg., USA) instead of dTTP, was incubated in 76 mM $K_2HPO_4$, 17 mM $KH_2PO_4$, 14 mM $NaH_2PO_4$, pH=7.2, 5 mM $MgCl_2$ and 1 mM ATP-γ-S withe 100 µg purified UvsXH6N2 or UvsXH6N2NIT-2 in a final volume of 200 µl for 30 min at room temparature. Then, 10 µl of each NPF reaction was applied to a 0.8% TAE/agarose gel which was subsequenty stained with ethidium bromide. The electrophoresis was carried out for 1 hour at 100 volts. FIG. 13 shows that the DNA was completely retarded. Thus, the DNA binding of the proteins is not hampered by the fluorescein labelling of the DNA.

Uptake of the NPFs in NIH3T3 cells by endocytosis:

NIH3T3 cells were plated in 6 well plates (3×10$^5$ per well), incubated over night at 37° C. and 5% $CO_2$, and were washed the next morning with prewarmed FCS-free medium; afterwards 2 ml FCS-free medium was added. 190 µl of the NPF reactions were added (see above), incubated for 30 min at room temperature, the supernatant was removed, the cells were washed and covered with 3 ml medium (with 10% FCS). After another incubation for 1 hour at 37° C. in the incubator, the analysis was carried out under the fluorescence microscope. In FIGS. 14a and 14b, one picture each is shown in bright field (lower) and reflected light fluorescence (upper)

In the bright field, vesicular intracellular compartments are visible which glow in the fluorescent light due to the endocytosed DNA (FIG. 14a, b, upper).

From each well, several pictures were taken. The cells were counted and the proportion of cells containing at least one fluorescent vesicular compartment was determined in percent (shown in FIG. 15). Each picture shows a mean of 35 cells.

Of the reactions with UvsXH6N2NIT-2, nine pictures were analyzed, and of the reactions with UvsXH6N2-2, five pictures were analyzed.

The result shows that the modification of UvsX with an integrin-binding motif as a functional component (UvsXH6N2-NIT-2) results in a markedly increased endocytotic uptake of the transfection agents in the cells compared to the control (UvsXH6N2-2).

EXAMPLE 11

Generation of a Transfection Agent Based on hRad51 as NPF-Forming Protein

The proteins hRad51H6 and hRad51H6N2 were used as NPF-forming proteins (see FIG. 16).

Structure of the Proteins hRad51 H6 (352 amino acids):

Amino acids 1-339: human Rad51 (NCBI protein accession no: Q06609, amino acids 1-339), amino acids 340-343: linker consisting of the amino acids $Y^{340}SYG^{343}$, amino acids 344-349: $H^{344}HHHHH^{349}$ for purification by nickel chelate affinity chromatography, amino acids 350-352: C-terminus consisting of the amino acids $M^{350}YS^{352}$.

hRad51 H6N2 (369 amino acids):

Amino acids 1-339: human Rad51 (NCBI protein accession no: Q06609, amino acids 1-339), amino acids 340-343: linker consisting of the amino acids $y^{340}SYG^{343}$, amino acids 344-349: $H^{344}HHHHH^{349}$ for purification by nickel chelate affinity chromatography, amino acids 350-352: linker consisting of the amino acids $M^{350}YS^{352}$, amino acids 353-366: nuclear localization signal nls-2 (amino acids 2-15, SEQ ID NO: 9 from WO 00/40742), amino acids 367-369: C-terminus consisting of the amino acids $G^{367}YP^{369}$.

Cloning of the Expression Plasmids

For expression of the above mentioned proteins in suitable *Escherichia coli* cells, plasmids were constructed that contain a coding sequence for hRad51H6 or hRad51 H6N2 under the control of the lac promoter (pExH-hRad51H6 or pExH-hRad51H6N2, see FIG. 16). pExH-UvsXH6-2 and pExH-UvsXH6N2-2 were used as source plasmids (see FIG. 16). The coding region for UvsX was cut out with EcoR V and BsiW I, and replaced by a PCR fragment with the coding region for hRad51 which had been cut out in the same way.

This was amplified from a human cDNA library using hRad51-specific primers that contain the desired restriction sites. At the 5'-end before the start codon, the PCR products contained the additional nucleotides 5'-CACACATCTA-GACGTACGGATATCAT-3' (SEQ ID NO:6'), and at their 3'-end they contained the additional nucleotides 5'-TACTCGTACGGAGGTGGCGGCCGCTGTGTG-3' (SEQ ID NO:7) instead of the stop codon.

Purification:

A preculture of 5 ml dYT/ampicillin (100 μg/ml) was inoculated with a colony of pExH-Rad51H6 or pExH-Rad51H6N2 in DH5, and was grown for 5 hours at 37° C. with 250 rpm. 10 l dYT/ampicillin (100 μg/ml) was inoculated with this preculture, and was allowed to grow for another 24 hours at 37° C. with 210 UPM. The cultures were harvested at 7000×g, and yielded apprpx. 30-50 g bacterial pellet. This was frozen for 1-3 days at −20° C. The pellet was thawed on ice, and resuspended in 100 ml cold starting buffer. The cells were then solubilized by ultrasound using a B. Braun Labsonic U (large probe, parameters: 300 watts, 0.5 sec pulse duration per second, 8 min sonification). Then it was incubated with 10 mg lysozyme (Serva, 190.000 u/mg) for 1 hours at 4° C. and for another 30 min after addition of 50 μl DNAse I (Serva, 2 mg/ml) with slow stirring. After removing the lysate by centrifugation (45 min, 18000×g, 4° C.), the supernatant was filtered through sterile filters (pore sizes 0.45 μm and 0.2 μm) and loaded on an equilibrated 1 ml HiTrapTM chelating column (Pharmacia) preloaded with Ni$^{++}$ ions. The further purification steps were carried out according to the respective Pharmacia protocol for proteins that have been provided with a histidine hexamer. Aliquots of the various elution fractions were applied to SDS/Coomassie gels. The purest fractions were combined and were further concentrated over Centriplus YM30 columns (Millipore) according to the respective protocol. Then it was dialyzed twice (dialysis tubing: Spectra/Por, MWCO: 25.000) against an at least one thousand-fold volume of ZI buffer for 1 hour each at 4° C., then over night at 4° C. against ZI buffer/50% glycerine. The dialysis product was aliquoted in 30-50 μl fractions and stored at −80° C. FIG. 17A shows the purified hRad51-H6 and hRad51-H6N2 proteins.

Used Buffer:

As in example 1, but different elution buffer: 20 mM Pi, 0.5 M NaCl, 100-1000 mM imidazole, pH=7.4

Determination of Concentration:

The concentrations of the hRad51 proteins was determined by measurement of the $OD_{280}$ using the extinction coefficient calculated with the Gene Inspector™ software (Textco, Inc.).

With hRad51H6 and hRad51H6N2 it was 11-13 μg/pl.

Description of the Experiment:

Binding of NLS-modified hRad51 to double-stranded DNA: hRad51H6N2purified over Ni$^{++}$-sepharose was incubated with 100 ng each of a 0.9 kb PCR fragment.

A DNA shift in the agarose gel caused by the protein binding shows that hRad51H6N2 cooperatively binds double-stranded DNA based on the concentration (FIG. 17B). Even with low amounts of hRad51H6N2, single DNA molecules are completely bound by hRad51H6N2, and are therefore retarded maximally, so that the retardation of the DNA does not increase any more by increasing the amount of protein. It is concluded that hRad51H6N2 binds dsDNA.

EXAMPLE 12

Generation of a Transfection Agent Based on UvsX With a Signal for the Non-Endosomal Membrane Permeation and a Nuclear Localization Signal as Functional Component As in example 1, a plasmid was generated that permits the expression of the fusion protein UvsXH6N2VP22c50 (see FIG. 1), which additionally contains a part of the tegument protein VP22 (gene UL49) of the human herpes virus 1 and is based on the protein UvsXH6N2-2 described in example 2. The here used VP22 peptide acts as a signal for the non-endosomal permeation through the cell membrane. Thus, the fusion protein UvsXH6N2VP22c50 contains a membrane transduction signal in addition to a nuclear localization signal (NSL).

Structure of the Protein

UvsXH6N2VP22c50 (474 amino acids):

Amino acids 1-391: UvsX from the phage T4 (NCBI protein accession no: AAD42669, amino acids 1-391), amino acids 392-394: linker consisting of the amino acids $S^{392}YG^{394}$, amino acids 395-400: $H^{395}HHHHH^{400}$, amino acids 401-403: linker consisting of the amino acids $M^{401}YS^{403}$, amino acids 404-417: nuclear localization signal nls-2 (amino acids 2-15, SEQ ID NO: 9 aus WO 00/40742), amino acids 418-422: linker consisting of the amino acids $G^{418}YPGS^{422}$, amino acids 423472: part of the tegument protein VP22 (Gen UL49) of the human herpes virus 1 (NCBI protein accession no: NP_044651, amino acids 252-301), amino acids 473-474: C-terminus consisting of the amino acids $P^{473}R^{474}$.

Cloning of the Expression Plasmid:

For the expression in suitable *Escherichia coli* cells, pExHUvsXH6N2-2 (see example 1 and FIG. 1) was opened by restriction enzyme digestion with Acc65 I and Spe I, and was ligated with a PCT product cut with Acc65 I and Nhe I, which contains at the 5'-end the additional nucleotides 5'-CACACAGGTACCCGGGATCC-3' (SEQ ID NO: 8) and at its 3'-end the additional nucleotides 5'-CCTAGG-TAATAATAAGCGGCCGCGCTAGCTGTGTG-3' (SEQ ID NO:9), in addition to the coding sequence for the last 50 amino acids of the tegument protein VP22 (gene UL49) of the human herpes virus 1 (NCBI nucleotide accession no: NC_001806, complementary sequence of the nucleotides 105486-106391) (see FIG. 1).

Purification:

The purification of UvsXH6N2VP22c50 was carried out as described in example 1 for H6UvsX (see FIG. 18A).

Concentration: 1.8 μg/μl.

Description of the Experiment:

Binding of a mixture of various modified UvsX (UvsX-NLS-VP22 and UvsX-NLS) to double-stranded DNA:

140 ng (in each case) of a purified 1.7 kb PCR fragments were incubated in 96 mM $K_2HPO_4$, 21.5 mM $KH_2PO_4$, 18 mM $NaH_2PO_4$, pH=7.2, 5 mM $MgCl_2$ and 1.3 mM ATP-γ-S with the amounts according to FIG. 18B of purified UvsXH6N2VP22c50 or UvsXH6N2-2 for 30 min at room temperature, then, all reactions were applied to a 0.8% TAE/agarose gel which was afterwards stained with ethidium bromide. The two proteins were different regarding their molecular weight and net charge, and therefore retarded the DNA differently during electrophoresis, with the complex with UvsXH6N2VP22c50 remaining stuck in the gel pocket and not migrating any more (see lanes 1 and 7 of FIG. 18B). When the proteins are mixed before they are added to the DNA, intermediate complexes are formed depending on the ratio of UvsXH6N2-2 and UvsXH6N2VP22c50, the migration performance of which is between those of the unmixed complexes (FIG. 18B). This shows that the DNA is occupied by both proteins. Also possible is a mixture of differently modified or one- or two-times modified NPF-forming proteins.

EXAMPLE 13

Transfection of a Cell Line (NIH3T3) With Complexes of DNA and a Mixture of UvsX-NLS-VP22 and UvsX-NLS Description of the Experiment:

$2.5 \times 10^5$ cells (NIH3T3) were plated out in each well of a 6-well plate, and transfected on the following day with a vector containing a gene for the expression of a fluorescent reporter protein. For this, 0 µg-1 µg linear or 1 µg circular DNA was preincubated with 36 µg UvsXH6N2VP22c50 or a mixture of 19 µg UvsXH6N2VP22c50 and 39 µg UvsXH6N2-2 in binding buffer (76 mM $K_2HPO_4$, 17 mM $KH_2PO_4$, 14 mM $NaH_2PO_4$, 5 mM $MgCl_2$, 1 mM ATP-γ-S, pH 7.21) for 30 min at room temperature, and together with 1 ml RPMI was added to cells that have before been washed once with PBS/BSA. After a 1 h incubation at 37° C., 5% $CO_2$ in the incubator, 1 ml RPMI/20% FCS was added respectively and further incubated in the incubator. 4 h or 24 h later, the cells were analyzed in the fluorescence microscope. Cells were observed that expressed the reporter gene after treatment with complexes of linear or circular DNA and the mixture of UvsXH6N2VP22c50 and UvsXH6N2-2 (see FIG. 19). The number of the transfected cells increased with the amount of used DNA or DNA-protein complexes.

However, no expression of the reporter gene was achieved with DNA complexes containing only UvsXH6N2VP22c50, or in absence of DNA.

Therefore it appears that by modification of an NPF-forming protein, here UvsX, with a membrane-active peptide, here VP22, the transfection of cells and here especially the membrane permeation is facilitated. The modular character of the method or transfection agent according to the invention is underlined by the combination of differently modified proteins, here modification with VP22 and NLS (see also FIG. 20). Whereas the VP22-modified UvsX permits the non-endosomal membrane permeation, the NLS-modified UvsX directs the transfected DNA from the cytoplasma to the nucleus; the transfected DNA can then be expressed there.

Thus, individual steps of the complex transfection procedure can be controlled specifically, flexible and with high efficiency in especially advantageous manner.

REFERENCES

Andersson, K. (1990). Codon Preferences in Free-Living Microorganisma. Micobiol Rev 54, 98-210.

Bal, H. P., Chroboczek, J., Schoehn, G., Ruigrok, R. W., and Dewhurst, S. (2000). Adenovirus type 7 penton purification of soluble pentamers from *Escherichia coli* and development of an integrin-dependent gene delivery system. Eur J Biochem 267, 6074-6081.

Baumann, P., and West, S.C. (1998). Role of the human RAD51 protein in homologous recombination and double-stranded-break repair. Trends Biochem Sci 23, 247-251.

Bianco, P. R., Tracy, R. B., and Kowalczykowski, S.C. (1998). DNA strand exchange proteins: a biochemical and physical comparison. Front Biosci 3, D570-603.

Boulikas, T. (1993). Nuclear localization signals (NLS). Crit Rev Eukaryot Gene Expr 3, 193-227.

Boulikas, T. (1996). Nuclear import of protein kinases and cyclins. J Cell Biochem 60, 61-82.

Boulikas, T. (1997). Nuclear import of DNA repair proteins. Anticancer Res 17, 843-863.

Cagnon, C., Valverde, V., and Masson, J. M. (1991). A new family of sugar-inducible expression vectors for *Escherichia coli*. Protein Eng 4, 843-847.

Cerutti, H., Osman, M., Grandoni, P., and Jagendorf, A. T. (1992). A homolog of *Escherichia coli* RecA protein in plastids of higher plants. Proc Natl Acad Sci USA 89, 8068-8072.

Collins, L., Sawyer, G. J., Zhang, X. H., Gustafsson, K., and Fabre, J. W. (2000). In vitro investigation of factors important for the delivery of an integrin-targeted nonviral DNA vector in organ transplantation. Transplantation 69, 1168-1176.

Delcayre, A. X., Salas, F., Mathur, S., Kovats, K., Lotz, M., and Lernhardt, W. (1991). Epstein Barr virus/complement C3d receptor is an interferon alpha receptor. Embo J 10, 919-926.

Di Capua, E., Engel, A., Stasiak, A., and Koller, T. (1982). Characterization of complexes between recA protein and duplex DNA by electron microscopy. J Mol Biol 157, 87-103.

Ellouze, C., Selmane, T., Kim, H. K., Tuite, E., Norden, B., Mortensen, K., and Takahashi, M. (1999). Difference between active and inactive nucleotide cofactors in the effect on the DNA binding and the helical structure of RecA filament dissociation of RecA—DNA complex by inactive nucleotides. Eur J Biochem 262, 88-94.

Evan, G. I., Lewis, G. K., Ramsay, G., and Bishop, J. M. (1985). Isolation of monoclonal antibodies specific for human c-myc proto-oncogene product. Mol Cell Biol 5, 3610-3616.

Feero, W. G., Li, S., Rosenblatt, J. D., Sirianni, N., Morgan, J. E., Partridge, T. A., Huang, L., and Hoffman, E. P. (1997). Selection and use of ligands for receptor-mediated gene delivery to myogenic cells. Gene Ther 4, 664-674.

Feldherr, C. M., and Akin, D. (1997). The location of the transport gate in the nuclear pore complex. J Cell Sci 110 (Pt 24), 3065-3070.

Fominaya, J., and Wels, W. (1996). Target cell-specific DNA transfer mediated by a chimeric multidomain protein. Novel non-viral gene delivery system. J Biol Chem 271, 10560-10568.

Griffith, J., Makhov, A., Santiago-Lara, L., and Setlow, P. (1994). Electron microscopic studies of the interaction between a *Bacillus subtilis* alpha/beta-type small, acid-soluble spore protein with DNA: protein binding is cooperative, stiffens the DNA, and induces negative supercoiling. Proc Natl Acad Sci USA 91, 8224-8228.

Harbottle, R. P., Cooper, R. G., Hart, S. L., Ladhoff, A., McKay, T., Knight, A. M., Wagner, E., Miller, A. D., and Coutelle, C. (1998). An RGD-oligolysine peptide: a prototype construct for integrin-mediated gene delivery. Hum Gene Ther 9, 1037-1047.

Hong, S. S., Gay, B., Karayan, L., Dabauvalle, M. C., and Boulanger, P. (1999). Cellular uptake and.nuclear delivery of recombinant adenovirus penton base. Virology 262, 163-177.

Karlin, S., and Brocchieri, L. (1996). Evolutionary conservation of RecA genes in relation to protein structure and function. J Bacteriol 178, 1881-1894.

Karlin, S., Weinstock, G. M., and Brendel, V. (1995). Bacterial classifications derived from recA protein sequence comparisons. J Bacteriol 177, 6881-6893.

Knight, K. L., and McEntee, K. (1985). Affinity labeling of a tyrosine residue in the ATP binding site of the recA protein from *Escherichia coli* with 5'-p-fluorosulfonylbenzoyladenosine. J Biol Chem 260, 10177-10184.

Kukowska-Latallo, J. F., Bielinska, A. U., Johnson, J., Spindler, R., Tomalia, D. A., and Baker, J. R., Jr. (1996). Efficient transfer of genetic material into mammalian cells using Starburst polyamidoamine dendrimers. Proc Natl Acad Sci USA 93, 4897-4902.

Lee, C. K., and Knipe, D. M. (1985). An immunoassay for the study of DNA-binding activities of herpes simplex virus protein ICP8. J Virol 54, 731-738.

Masson, J. Y., Davies, A. A., Hajibagheri, N., Van Dyck, E., Benson, F. E., Stasiak, A. Z., Stasiak, A., and West, S.C. (1999). The meiosis-specific recombinase hDmc1 forms ring structures and interacts with hRad51. Embo J 18, 6552-6560.

Mengaud, J., Ohayon, H., Gounon, P., Mege, R. M., and Cossart, P. (1996). E-cadherin is the receptor for internalin, a surface protein required for entry of L. monocytogenes into epithelial cells. Cell 84, 923-932.

Midoux, P., Mendes, C., Legrand, A., Raimond, J., Mayer, R., Monsigny, M., and Roche, A. C. (1993). Specific gene transfer mediated by lactosylated poly-L-lysine into hepatoma cells. Nucleic Acids Res 21, 871-878.

Mosig, G. (1987). The essential role of recombination in phage T4 growth. Annu Rev Genet 21, 347-371.

Neumann, G., Castrucci, M. R., and Kawaoka, Y. (1997). Nuclear import and export of influenza virus nucleoprotein. J Virol 71, 9690-9700.

Ogawa, T., Shinohara, A., Nabetani, A., Ikeya, T., Yu, X., Egelman, E. H., and Ogawa, H. (1993). RecA-like recombination proteins in eukaryotes: functions and structures of RAD51 genes. Cold Spring Harb Symp Quant Biol 58, 567-576.

Ohno, K., Sawai, K., Iijima, Y., Levin, B., and Meruelo, D. (1997). Cell-specific targeting of Sindbis virus vectors displaying IgG-binding domains of protein A. Nat Biotechnol 15, 763-767.

Pack, D. W., Putnam, D., and Langer, R. (2000). Design of imidazole-containing endosomolytic biopolymers for gene delivery. Biotechnol Bioeng 67, 217-223.

Plow, E. F., Haas, T. A., Zhang, L., Loftus, J., and Smith, J. W. (2000). Ligand binding to integrins. J Biol Chem 275, 21785-21788.

Pooga, M., Soomets, U., Hallbrink, M., Valkna, A., Saar, K., Rezaei, K., Kahi, U., Hao, J. X., Xu, X. J., Wiesenfeld-Hallin, Z., et al. (1998). Cell penetrating PNA constructs regulate galanin receptor levels and modify pain transmission in vivo. Nat Biotechnol 16, 857-861.

Provoda, C. J., and Lee, K. D. (2000). Bacterial pore-forming hemolysins and their use in the cytosolic delivery of macromolecules. Adv Drug Deliv Rev 41, 209-221.

Richardson, S., Ferruti, P., and Duncan, R. (1999). Poly (amidoamine)s as potential endosomolytic polymers: evaluation in vitro and body distribution in normal and tumour-bearing animals. J Drug Target 6, 391-404.

Roca, A. I., and Cox, M. M. (1990). The RecA protein: structure and function. Crit Rev Biochem Mol Biol 25, 415-456.

Rosenkranz, A. A., Yachmenev, S. V., Jans, D. A., Serebryakova, N. V., Murav'ev, V. I., Peters, R., and Sobolev, A. S. (1992). Receptor-mediated endocytosis and nuclear transport of a transfecting DNA construct. Exp Cell Res 199, 323-329.

Sandier, S. J., Satin, L. H., Samra, H. S., and Clark, A. J. (1996). recA-like genes from three archaean species with putative protein products similar to Rad51 and Dmc1 proteins of the yeast *Saccharomyces cerevisiae*. Nucleic Acids Res 24, 2125-2132.

Schagger, H., and von Jagow, G. (1987). Tricine-Sodium Dodecyl Sulfate-Polyacrylamide Gel Electrophoresis for the Separation of Proteins in the Range from 1 to 100 kDa. Anal Biochem 166, 368-379.

Schoeman, R., Joubert, D., Ariatti, M., and Hawtrey, A. O. (1995). Further studies on targeted DNA transfer to cells using a highly efficient delivery system of biotinylated transferrin and biotinylated polylysine complexed to streptavidin. J Drug Target 2, 509-516.

Seitz, E. M., Brockman, J. P., Sandler, S. J., Clark, A. J., and Kowalczykowski, S.C. (1998). RadA protein is an archaeal RecA protein homolog that catalyzes DNA strand exchange. Genes Dev 12, 1248-1253.

Steinhauer, D. A., Wharton, S. A., Skehel, J. J., and Wiley, D.C. (1995). Studies of the membrane fusion activities of fusion peptide mutants of influenza virus hemagglutinin. J Virol 69, 6643-6651.

Surdej, P., and Jacobs-Lorena, M. (1994). Strategy for epitope tagging the protein-coding region of any gene. Biotechniques 17, 560-565.

Tang, M. X., and Szoka, F. C. (1997). The influence of polymer structure on the interactions of cationic polymers with DNA and morphology of the resulting complexes. Gene Ther 4, 823-832.

Thoren, P. E., Persson, D., Karlsson, M., and Norden, B. (2000). The antennapedia peptide penetratin translocates across lipid bilayers—the first direct observation. FEBS Lett 482, 265-268.

Thyagarajan, B., Padua, R. A., and Campbell, C. (1996). Mammalian mitochondria possess homologous DNA recombination activity. J Biol Chem 271, 27536-27543.

Wagner, E. (1999). Application of membrane-active peptides for nonviral gene delivery. Adv Drug Deliv Rev 38, 279-289.

Wang, P., Palese, P., and O'Neill, R. E. (1997). The NPI-1/NPI-3 (karyopherin alpha) binding site on the influenza a virus nucleoprotein NP is a nonconventional nuclear localization signal. J Virol 71, 1850-1856.

Weisbart, R. H., Baldwin, R., Huh, B., Zack, D. J., and Nishimura, R. (2000). Novel protein transfection of primary rat cortical neurons using an antibody that penetrates living cells. J Immunol 164, 6020-6026.

Yamada, M., and Kasamatsu, H. (1993). Role of nuclear pore complex in simian virus 40 nuclear targeting. J Virol 67,119-130.

Yu, X., and Egelman, E. H. (1993). DNA conformation induced by the bacteriophage T4 UvsX protein appears identical to the conformation induced by the *Escherichia coli* RecA protein. J Mol Biol 232, 1-4.

Zauner, W., Blaas, D., Kuechler, E., and Wagner, E. (1995). Rhinovirus-mediated endosomal release of transfection complexes. J Virol 69, 1085-1092.

The invention claimed is:

1. A method for transfection of cells using at least one protein capable of forming nucleoprotein filaments, wherein the protein is initially modified with at least two functional components of different function, and/or wherein different proteins are each initially modified with components of different function, each functional component influencing one or more steps of the transfection, a nucleic acid to be transfected is then loaded with the modified protein, the nucleic acid and the protein forming a filament-like complex, and this complex is added to the cells to be transfected, wherein
   a. the protein binds a nucleic acid sequence and forms a nucleoprotein filament, and
   b. the protein so modified is modified by the addition of any of a functional component which causes association of the complex to the cellular surface, endosomal or non-endosomal passage of the complex through the cell membrane, release of the complex from endosomes or lysosomes, transport of the complex into the nucleus, or combination thereof,
   thereby facilitating transfection.

2. The method of claim 1, wherein the protein is modified with a plurality of functional components.

3. The method of claim 1, wherein the complex is stabilized by addition of nucleoside triphosphates and/or non-hydrolyzable analogues thereof.

4. The method of claim 1 being employed in combination with other biological and/or chemical and/or physical transfection methods for nucleic acids.

5. A transfection agent containing a nucleoprotein filament, wherein the nucleoprotein filament is formed of at least one nucleic acid to be transfected and at least one protein being capable of forming nucleoprotein filaments, wherein the protein that is capable of forming nucleoprotein filaments is modified with at least two functional components of different function, and/or wherein different proteins that are capable of forming nucleoprotein filaments are each modified with components of different function, each functional component influencing one or more steps of the transfection, wherein
   a. the protein binds a nucleic acid sequence and forms a nucleoprotein filament, and
   b. the protein so modified is modified by the addition of any of a functional component which causes association of the complex to the cellular surface, endosomal or non-endosomal passage of the complex through the cell membrane, release of the complex from endosomes or lysosomes, transport of the complex into the nucleus, or combination thereof,
   thereby facilitating transfection.

6. The transfection agent according to claim 5, wherein the protein is modified with a plurality of functional components.

7. The transfection agent of claim 5 containing, as the filament-forming protein, a protein of (a) selected from the group of the proteins RecA, RadA, RAD51, hDmcl, SASP, ICP8, UvsX, hRAD51 or a mixture of at least 2 of the listed proteins or derivatives thereof.

8. A kit, suitable for transfection of cells with nucleic acids, comprising at least one protein capable of forming nucleoprotein filaments, and at least one functional component influencing one or more steps of transfection, as well as at least one of the following components:
   a) nucleoside triphosphate and/or nucleoside triphosphate analogues,
   b) at least one nucleic acid to be transfected,
   c) adjuvants and additives,
wherein the protein binds a nucleic acid sequence and forms a nucleoprotein filament, and the protein so modified is modified by the addition of any of a functional component which causes association of the complex to the cellular surface, endosomal or non-endosomal passage of the complex through the cell membrane, release of the complex from endosomes or lysosomes, transport of the complex into the nucleus, or combination thereof, thereby facilitating transfection.

9. A method for identification of activators or inhibitors of the expression product(s) of the transfection agent of claim 5 wherein a cell is transfected with the transfection agent and exposed to potential inhibitors or activators.

10. A method for identification of physiologically active nucleic acids, wherein cells are transfected with the transfection agent of claim 5 and physiological modifications are determined in comparison with untransfected control cells.

11. The method of claim 1, wherein the protein of (a) is selected from the group of RecA, RadA, RAD51, hDmcl, SASP, ICP8, UvsX, hRAD51 or a mixture of at least 2 of the listed proteins or derivatives thereof.

12. The method of claim 1, wherein the modification is one or more of an amino acid linker, Nuclear Localization Signal (NLS), ligand to the Epstein Barr Virus receptor CD21, ligand to Listeria monocytogenes receptor E-cadherin, ligand to transferrin receptor/transferrin, ligand to asialoglycoprotein receptor, integrin-binding peptides, ligand to insulin receptor, ligand to EGF (epidermal growth factor) receptor, ligand to insulin-like growth factor I receptor, ligand to lectins, protein A or its IgG-binding domain, epitope from the influenza hemagglutinin, epitope from the c-myc protein, peptides from HIV tat, peptides from VP22, peptides from HBV surface antigen, peptides from homeodomain of antennapedia, peptides from engrailed, peptides from HOXA-5, peptides from IL-1.beta., peptides from FGF-1, peptides from FGF-2, peptides from Kaposi fibroblast growth factor, mab 3E10, transportane, peptides from streptolysin O, peptides from pneumolysin, peptides from staphylococcal .alpha.-toxin, peptides from listeriolysin O, peptides from the N-terminal hemagglutinin HA-2 peptide of influenza virus, peptides from the N-terminus of the VP-1 protein of rhinovirus HRV2, peptides from the capsid component Ad2 of adenovirus, amphipathic peptide GALA, amphipathic peptide KALA, amphipathic peptide EGLA, amphipathic peptide JTS 1, imidazole or polyamidoamine-modified polymers.

13. The kit of claim 8 containing, as the nucleoprotein filament-forming protein, a protein selected from the group of RecA, RadA, RAD51, hDmcl, SASP, ICP8, UvsX, hRAD51 or a mixture of at least 2 of the listed proteins or derivatives thereof.

14. The transfection agent of claim 5, wherein the modification is one or more of an amino acid linker, Nuclear Localization Signal (NLS), ligand to the Epstein Barr Virus receptor CD21, ligand to Listeria monocytogenes receptor E-cadherin, ligand to transferrin receptor/transferrin, ligand to asialoglycoprotein receptor, integrin-binding peptides, ligand to insulin receptor, ligand to EGF (epidermal growth factor) receptor, ligand to insulin-like growth factor I receptor, ligand to lectins, protein A or its IgG-binding domain, epitope from the influenza hemagglutinin, epitope from the c-myc protein, peptides from HIV tat, peptides from VP22, peptides from HBV surface antigen, peptides from homeodomain of antennapedia, peptides from engrailed, peptides from HOXA-5, peptides from IL-1.beta., peptides from FGF-1, peptides from FGF-2, peptides from Kaposi fibroblast growth factor, mab 3E10, transportane, peptides from streptolysin O, peptides from pneumolysin, peptides from staphylococcal .alpha.-toxin, peptides from listeriolysin O, peptides from the N-terminal hemagglutinin HA-2 peptide of influenza virus, peptides from the N-terminus of the VP-1 protein of rhinovirus HRV2, peptides from the capsid component Ad2 of adenovirus, amphipathic peptide GALA, amphipathic peptide KALA, amphipatilic peptide EGLA, amphipathic peptide JTSI, imidazole or polyamidoamine-modified polymers.

15. The kit of claim 8, wherein the protein that forms a nucleoprotein filament is modified with one or more of an amino acid linker, Nuclear Localization Signal (NLS), ligand to the Epstein Barr Virus receptor CD21, ligand to Listeria monocytogenes receptor E-cadherin, ligand to transferrin receptor/transferrin, ligand to asialoglycoprotein receptor, integrin-binding peptides, ligand to insulin receptor, ligand to EGF (epidermal growth factor) receptor, ligand to insulin-like growth factor I receptor, ligand to lectins, protein A or its IgG-binding domain, epitope from the influenza hemagglutinin, epitope from the c-myc protein, peptides from HIV tat, peptides from VP22, peptides from HBV surface antigen, peptides from homeodomain of antennapedia, peptides from engrailed, peptides from HOXA-5, peptides from IL-l.beta, peptides from FGF-1, peptides from FGF-2, peptides from Kaposi fibroblast growth factor, mab 3E10, transportane, peptides from streptolysin O, peptides from pneumolysin, peptides from staphylococcal .alpha.-toxin, peptides from listeriolysin O, peptides from the N-terminal hemagglutinin HA-2 peptide of influenza virus, peptides from the N-terminus of the VP-1 protein of rhinovirus HRV2, peptides from the capsid component Ad2 of adenovirus, amphipathic peptide GALA, amphipathic peptide I~ALA, amphipathic peptide EGLA, amphipathic peptide TTSI, imidazole or polyamidoamine-modified polymers.

* * * * *